(12) United States Patent
Pang et al.

(10) Patent No.: US 8,492,428 B2
(45) Date of Patent: Jul. 23, 2013

(54) SMALL-MOLECULE BOTULINUM TOXIN INHIBITORS

(75) Inventors: Yuan-Ping Pang, Rochester, MN (US);
Jewn Giew Park, Rochester, MN (US);
Jing Tang, Rochester, MN (US);
Charles B. Millard, Frederick, MD (US); James J. Schmidt, Mt. Airy, MD (US)

(73) Assignees: Mayo Foundation for Medical Education and Research, Rochester, MN (US); The United States of America As Represented by the Secretary of the Army, Washington, DC (US)

( * ) Notice: Subject to any disclaimer, the term of this patent is extended or adjusted under 35 U.S.C. 154(b) by 823 days.

(21) Appl. No.: 12/067,158

(22) PCT Filed: Sep. 20, 2006

(86) PCT No.: PCT/US2006/036710
§ 371 (c)(1),
(2), (4) Date: Jun. 7, 2010

(87) PCT Pub. No.: WO2008/051197
PCT Pub. Date: May 2, 2008

(65) Prior Publication Data
US 2010/0260778 A1    Oct. 14, 2010

Related U.S. Application Data

(60) Provisional application No. 60/718,763, filed on Sep. 20, 2005.

(51) Int. Cl.
*A61K 31/404* (2006.01)
*C07D 209/08* (2006.01)
*C07D 401/14* (2006.01)
*C07D 403/14* (2006.01)

(52) U.S. Cl.
USPC ......... 514/414; 544/333; 546/277.4; 548/468

(58) Field of Classification Search
USPC .................. 544/333; 546/277.4; 548/468
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,710,795 A | 1/1973 | Higuchi et al. | |
| 3,845,770 A | 11/1974 | Theeuwes et al. | |
| 3,916,899 A | 11/1975 | Theeuwes et al. | |
| RE28,819 E | 5/1976 | Thompson | |
| 4,008,719 A | 2/1977 | Theeuwes et al. | |
| 4,044,126 A | 8/1977 | Cook et al. | |
| 4,328,245 A | 5/1982 | Yu et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu et al. | |
| 4,414,209 A | 11/1983 | Cook et al. | |
| 4,522,811 A | 6/1985 | Eppstein et al. | |
| 4,710,384 A | 12/1987 | Rotman | |
| 5,033,252 A | 7/1991 | Carter | |
| 5,052,558 A | 10/1991 | Carter | |
| 5,059,595 A | 10/1991 | Le Grazie | |
| 5,073,543 A | 12/1991 | Marshall et al. | |
| 5,120,548 A | 6/1992 | McClelland et al. | |
| 5,323,907 A | 6/1994 | Kalvelage | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,709,874 A | 1/1998 | Hanson et al. | |
| 5,733,566 A | 3/1998 | Lewis | |
| 5,759,542 A | 6/1998 | Gurewich | |
| 5,840,674 A | 11/1998 | Yatvin et al. | |
| 5,860,957 A | 1/1999 | Jacobsen et al. | |
| 5,900,252 A | 5/1999 | Calanchi et al. | |
| 5,948,433 A | 9/1999 | Burton et al. | |
| 5,972,366 A | 10/1999 | Haynes et al. | |
| 5,983,134 A | 11/1999 | Ostrow | |
| 5,985,307 A | 11/1999 | Hanson et al. | |
| 5,985,317 A | 11/1999 | Venkateshwaran | |
| 6,004,534 A | 12/1999 | Langer et al. | |
| 6,010,715 A | 1/2000 | Wick et al. | |
| 6,024,975 A | 2/2000 | D'Angelo et al. | |
| 6,039,975 A | 3/2000 | Shah et al. | |
| 6,048,736 A | 4/2000 | Kosak | |
| 6,060,082 A | 5/2000 | Chen et al. | |
| 6,071,495 A | 6/2000 | Unger et al. | |
| 6,120,751 A | 9/2000 | Unger | |
| 6,131,570 A | 10/2000 | Schuster et al. | |
| 6,139,865 A | 10/2000 | Friend et al. | |
| 6,167,301 A | 12/2000 | Flower et al. | |
| 6,253,872 B1 | 7/2001 | Neumann | |
| 6,256,533 B1 | 7/2001 | Yuzhakov et al. | |
| 6,261,595 B1 | 7/2001 | Stanley et al. | |
| 6,267,983 B1 | 7/2001 | Fujii et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,753,344 B2 | 6/2004 | Talley et al. | |
| 2004/0176333 A1 | 9/2004 | Roques et al. | |

(Continued)

FOREIGN PATENT DOCUMENTS

DE    4 325 204    11/2002
DE    10 236 340    2/2004

(Continued)

OTHER PUBLICATIONS

Vippagunta, et al. Advanced Drug Delivery Reviews 48 (2001) 3-26.*

(Continued)

*Primary Examiner* — Shawquia Young
(74) *Attorney, Agent, or Firm* — Fish & Richardson P.C.

(57) ABSTRACT

Small-molecule inhibitors of Botulinum toxin, including BoNTA, BoNTD and BoNTE are provided, as well as methods of using the inhibitors.

20 Claims, 9 Drawing Sheets

FOREIGN PATENT DOCUMENTS

| | | |
|---|---|---|
| EP | 405 602 | 1/1991 |
| EP | 389 699 | 5/1994 |
| EP | 1 233 016 | 8/2002 |
| ES | 2 016 474 | 11/1990 |
| ES | 2 016 503 | 11/1990 |
| SU | 753 091 | 2/1985 |
| SU | 1 031 165 | 11/1985 |
| WO | WO 93/09085 | 5/1993 |
| WO | WO 98/06691 | 2/1998 |
| WO | WO 01/28557 | 4/2001 |
| WO | WO 03/097644 | 11/2003 |
| WO | WO 2004/035570 | 4/2004 |
| WO | WO 2004/056368 | 7/2004 |

OTHER PUBLICATIONS

Blommaert, et al. Bioorganic & Medicinal Chemistry (2004) 12, 3055-3062.*

Schmidt et al., "Type A botulinum neurotoxin proteolytic activity: development of competitive inhibitors and implications for substrate specificity at the $S_1$' binding subsite," FEBS Lett., 1998, 435:61-64.

Tacket et al., "Equine Antitoxin Use and Other Factors That Predict Outcome in Type A Foodborne Botulism," Am. J. Med., 1984, 76:794-798.

Abbenante and Fairlie, "Protease Inhibitors in the Clinic," Med. Chem., 2005, 1:71-104.

Anne et al., "Thio-Derived Disulfides as Potent Inhibitors of Botulinum Neurotoxin Type B: Implications for Zinc Interaction," Bioorg. Med. Chem., 2003, 11:4655-4660.

Anne et al., "Development of Potent Inhibitors of Botulinum Neurotoxin Type B," J. Med. Chem., 2003, 46:4648-4656.

Aqvist and Warshel, "Free Energy Relationships in Metalloenzyme-Catalyzed Reactions. Calculations of the Effects of Metal Ion Substitutions in Staphylococcal Nuclease," J. Am. Chem. Soc., 1990, 112:2860-2868.

Arcadi et al., "Palladium-Catalysed Coupling of Aryl and Vinyl Triflates or Halides with 2-Ethynylaniline: An Efficient Route to Functionalized 2-Substituted Indoles," Tetrahedron Lett., 1989, 30(19):2581-2584.

Arkin and Wells, "Small-Molecule Inhibitors of Protein-Protein Interactions: Progressing Towards the Dream," Nat. Rev. Drug Disc., 2004, 3:301-317.

Bellamy and Ou, "Selective Reduction of Aromatic Nitro Compounds with Stannous Chloride in Non Acidic and Non Aqueous Medium," Tetrahedron Lett., 1984, 25(8):839-842.

Berendsen et al., "Molecular dynamics with coupling to an external bath," J. Chem. Phys., 1984, 81(8):3684-3690

Berweger et al., "Molecular-Dynamics Simulation of the β Domain of Metallothionein With a Semi-Empirical Treatment of the Metal Core," Proteins, 2000, 41:299-315.

Blommaert et al., "Small tripeptide surrogates with low nanomolar affinity as potent inhibitors of the Botulinum neurotoxin B metalloproteolytic activity," Bioorg. Med. Chem., 2004, 12:3055-3062.

Breidenbach and Brunger, "Substrate recognition strategy for Botulinum neurotoxin serotype A," Nature, 2004, 432:925-929.

Brown et al., "Quest for Selectivity in Inhibition of Matrix Metalloproteinases," Curr. Top. Med. Chem., 2004, 4:1227-1238.

Burnett et al., "Novel small molecule inhibitors of botulinum neurotoxin A metalloprotease activity," Biochem. Biophys. Res. Commun., 2003, 310:84-93.

Cornell et al., "A Second Generation Force Field for the Simulation of Proteins, Nucleic Acids, and Organic Molecules," J. Am. Chem. Soc., 1995, 117:5179-5197.

Darden et al., "Particle mesh Ewald: An $N\cdot\log(N)$ method for Ewald sums in large systems," J. Chem. Phys., 1993, 98(12):10089-10092.

El Yazal and Pang, "Comparison of DFT, Moller-Plesset, and coupled cluster calculations of the proton dissociation energies of imidazole and N-methylacetamide in the presence of zinc(II)," J. Mol. Struct., 2001, 545:271-274.

El Yazal and Pang, "Ab Initio Calculations of Proton Dissociation Energies of Zinc Ligands: Hypothesis of Imidazolate as Zinc Ligand in Proteins," J. Phys. Chem. B, 1999, 103:8773-8779.

El Yazal and Pang, "Proton Dissociation Energies of Zinc-Coordinated Hydroxamic Acids and Their Relative Affinities for Zinc: Insight into Design of Inhibitors of Zinc-Containing Proteinases," J. Phys. Chem. B, 2000, 104:6499-6504.

El Yazal et al., "Zinc's Affect on Proton Transfer between Imidazole and Acetate Predicted by ab Initio Calculations," J. Phys. Chem. B, 2000, 104:6662-6667.

Eswaramoorthy et al., "Crystallographic evidence for doxorubicin binding to the receptor-binding site in Clostridium botulinum neurotoxin B," Acta Cryst., 2001, D57:1743-1746.

Fedorova et al., "Synthesis and Antimicrobial Activity of 5-Hydroxynaphtho [1,2-b] Thiophenes and 4-hydroxybenzo [2,1-b:3,4-b']Dithiophenes," Pharm. Chem. J., 1987, 21:772-777.

Hanson and Stevens, "Cocrystal structure of synaptobrevin-II bound to botulinum neurotoxin type B at 2.0 Å resolution," Nat. Struct. Biol., 2000, 7(8):687-692.

Hayat et al., N-Alkylation of anilines, carboxamides and several nitrogen heterocycles using CsF-Celite/alkyl halides/$CH_3CN$ combination, Tetrahedron, 2001, 57:9951-9957.

Hoops et al., "Force Field Design for Metalloproteins," J. Am. Chem. Soc., 1991, 113:8262-8270.

Jorgensen et al., "Comparison of simple potential functions for simulating liquid water," J. Chem. Phys., 1983, 79(2):926-935.

Katz et al., "Design of potent selective zinc-mediated serine protease inhibitors," Nature, 1998, 391:608-612.

Kessler and Benecke, "Botulinum Toxin: From Poison to Remedy," NeuroToxicology, 1997, 18(3):761-770.

Lacy et al., "Crystal structure of Botulinum neurotoxin type A and implications for toxicity," Nat. Struct. Biol., 1998, 5(10):898-902.

Lightstone et al., "Identification of Novel Small Molecule Ligands That Bind to Tetanus Toxin," Chem. Res. Toxicol., 2000, 13:356-362.

Lu and Voth, "Molecular Dynamics Simulations of Human Carbonic Anhydrase II: Insight Into Experimental Results and the Role of Solvation," Proteins, 1998, 33:119-134.

Matter and Schudok, "Recent advances in the design of matrix metalloprotease inhibitors," Curr. Opin. Drug Disc. Dev., 2004, 7(4):513-535.

McMillan et al., "Allosteric inhibitors of inducible nitric oxide synthase dimerization discovered via combinatorial chemistry," Proc. Natl. Acad. Sci. USA, 2000, 97(4):1506-1511.

Miyamoto and Kollrnan, "SETTLE: An Analytical Version of the SHAKE and RATTLE Algorithm for Rigid Water Models," J. Comp. Chem., 1992, 13:952-962.

Montecucco et al., "Bacterial protein toxins penetrate cells via a four-step mechanism," FEBS Lett., 1994, 346:92-98.

Oelschlaeger et al., "Insight into the mechanism of the IMP-1 metallo-β-lactamase by molecular dynamics simulations," Protein Eng., 2003, 16(5):341-350.

Oelschlaeger et al., "Modeling Domino Effects in Enzymes: Molecular Basis of the Substrate Specificity of the Bacterial Metallo-β-lactamases IMP-1 and IMP-6,"Biochemistry, 2003, 42:8945-8956.

Pang et al., "Computational and Experimental Studies of (2,2)-Bis(indo1-1-yl-methyl)acetate Suggest the Importance of the Hydrophobic Effect in Aromatic Stacking Interactions," J. Am. Chem. Soc., 1999, 121:1717-1725.

Pang, "Novel Zinc Protein Molecular Dynamics Simulations: Steps Toward Antiangiogenesis for Cancer Treatment," J. Mol. Model., 1999, 5:196-202.

Pang et al., "EUDOC: A Computer Program Identification of Drug Interaction Sites in Macromolecules and Drug Leads from Chemical Databases," J. Comp. Chem., 2001, 22(15):1750-1771.

Pang et al., "Successful molecular dynamics simulation of the zinc-bound farnesyltransferase using the cationic dummy atom approach," Protein Sci., 2000, 9:1857-1865.

Pang, "Successful Molecular Dynamics Simulation of Two Zinc Complexes Bridged by a Hydroxide in Phosphotriesterase Using the Cationic Dummy Atom Method," Proteins, 2001, 45:183-189.

Pang, "Three-Dimensional Model of a Substrate-Bound SARS Chymotrypsin-Like Cysteine Proteinase Predicted by Multiple Molecular Dynamics Simulations: Catalytic Efficiency Regulated by Substrate Binding," Proteins, 2004, 57:747-757.

Park et al., "Serotype-selective, small-molecule inhibitors of the zinc endopeptidase of botulinum neurotoxin serotype A," *Bioorg. Med. Chem.*, 2006, 14(2):395-408.

Pearlman et al., "AMBER, a package of computer programs for applying molecular mechanics, normal mode analysis, molecular dynamics and free energy calculations to simulate the structural and energetic properties of molecules," *Comput. Phys. Commun.*, 1995, 91:1-41.

Perola et al., "Successful Virtual Screening of a Chemical Database for Farnesyltransferase Inhibitor Leads," *J. Med. Chem.*, 2000, 43:401-408.

Roe and Pang, "Zinc's Exclusive Tetrahedral Coordination Governed by Its Electronic Structure," *J. Mol. Model.*, 1999, 5:134-140.

Rossello et al., "New N-arylsulfonyl-N-alkoxyaminoacetohydroxamic acids as selective inhibitors of gelatinase A (MMP-2)," *Bioorg. Med. Chem.*, 2004, 12:2441-2450.

Rush and Powers, "The Application of X-ray, NMR, and Molecular Modeling in the Design of MMP Inhibitors," *Curr. Top. Med. Chem.*, 2004, 4:1311-1327.

Ryde, "Molecular Dynamics Simulations of Alcohol Dehydrogenase With a Four- or Five-Coordinate Catalytic Zinc Ion," *Proteins*, 1995, 21:40-56.

Sakai et al., "Palladium-Catalyzed Coupling Reaction of Terminal Alkynes with Aryl Iodides in the Presence of Indium Tribromide and its Application to a One-Pot Synthesis of 2-Phenylindole," *Org. Lett.*, 2004, 6(10):1527-1530.

Schmidt and Bostian, "Endoproteinase Activity of Type A Botulinum Neurotoxin: Substrate Requirements and Activation by Serum Albumin," *J. Protein Chem.*, 1997, 16:19-26.

Schmidt and Stafford, "A high-affinity competitive inhibitor of type A botulinum neurotoxin protease activity," *FEBS Lett.*, 2002, 532:423-426.

Schmidt and Stafford, "Fluorigenic Substrates for the Protease Activities of Botulinum Neurotoxins, Serotypes A, B, and F," *Appl. Environ. Microbiol.*, 2003, 69:297-303.

Shapiro et al., "Botulism in the United States: A Clinical and Epidemiologic Review," *Ann. Intern. Med.*, 1998, 129(3):221-228.

Shone and Roberts, "Peptide substrate specificity and properties of the zinc-endopeptidase activity of botulinum type B neurotoxin," *Eur. J. Biochem.*, 1994, 225:263-270.

Shvedov and Fedorova, "The Vilsmeier Reaction in the Series of Esters of Alkyl, Aryl, and Heteryl Keto Acids," *J. Org. Chem. USSR*, 1991, 27:210-213.

Simpson, "The Origin, Structure, and Pharmacological Activity of Botulinum Toxin," *Pharmacol. Rev.*, 1981, 33(3):155-188.

Singh, "Intimate details of the most poisonous poison," *Nat. Struct. Biol.*, 2000, 7(8):617-619.

Springen et al., "Certified Organic," *Newsweek*, 2002, 4 pages.

Sukonpan et al., "Synthesis of substrates and inhibitors of botulinum neurotoxin type A metalloprotease," *J. Pept. Res.*, 2004, 63:181-193.

Thouin and Lubell, "Effective synthesis of enantiopure hydroxamates by displacement of resin-bound esters with hydroxylamine," *Tetrahedron Lett.*, 2000, 41:457-460.

Yamamoto et al., "Inhibition of Membrane-Type 1 Matrix Metalloproteinase by Hydroxamate Inhibitors: An Examination of the Subsite Pocket," *J. Med. Chem.*, 1998, 41:1209-1217.

* cited by examiner

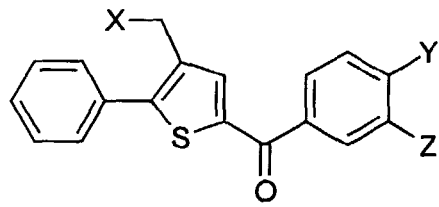

1. X = CO₂H, Y = Cl, Z = H, 15±0(1)% inhibition
2. X = CONHOH, Y = Cl, Z = H, 30±1(2)% inhibition
3. X = CONHOH, Y = Br, Z = H, 11±2(2)% inhibition
4. X = CONHOH, Y = I, Z = NH₂, 40±3(3)% inhibition
5. X = CONHOH, Y = I, Z = NO₂, 3±1(2)% inhibition
6. X = CONHNH₂, Y = Br, Z = H, 5±1(2)% inhibition
7. X = CONHNH₂, Y = I, Z = NH₂, 4±1(2)% inhibition

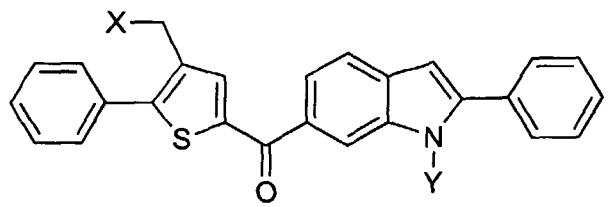

8. X = CO₂H, Y = H, 10±0(2)% inhibition
9. X = CONHOH, Y = H, 4±1(2)% inhibition
10. X = CO₂H, Y = (CH₂)₄NH₂, 30±1(2)% inhibition
11. X = CONHNH₂, Y = (CH₂)₄NH₂, 89±0(2)% inhibition
12. X = CONHOH, Y = (CH₂)₄NH₂, 96±6(2)% inhibition
13. X = CONHOH, Y = (CH₂)₅NH₂, 96±4(2)% inhibition
14. X = CONHOH, Y = (CH₂)₆NH₂, 97±2(2)% inhibition

FIG. 1

SMALL-MOLECULE BOTULINUM TOXIN INHIBITORS

CROSS-REFERENCE TO RELATED APPLICATION

This application is a National Stage application under 35 U.S.C. §371 and claims the benefit under 35 U.S.C. §119(a) of International Application No. PCT/US2006/036710, having an International Filing Date of Sep. 20, 2006, which claims the benefit of priority of the U.S. Provisional Application Ser. No. 60/718,763, having a filing date of Sep. 20, 2005, all of which are incorporated herein in their entirety.

STATEMENT AS TO FEDERALLY FUNDED RESEARCH

Studies described herein were supported by the U.S. Army Medical Research Acquisition Activity (W81XWH-04-2-0001). The Government has certain rights in this invention.

TECHNICAL FIELD

This disclosure relates to materials and methods for inhibiting Botulinum neurotoxin, and more particularly to materials and methods for inhibiting the zinc endopeptidase of Botulinum neurotoxin serotypes A, D and/or E (BoNTA, BoNTD and/or BoNTE).

BACKGROUND

Botulinum neurotoxin serotype A (BoNTA) is a highly toxic by-product of a naturally occurring, spore-forming anaerobic bacterium (*Clostridium botulinum*). BoNTA inhibits the release of acetylcholine from presynaptic nerve terminals at neuromuscular junctions, causing flaccid paralysis and leading to death by respiratory arrest. BoNTA also can be used in the treatment of various muscular dysfunctions and has been widely used as a cosmetic known as Botox to diminish facial lines. BoNTA, however, is fatal when misused, and there are currently no chemical antidotes to BoNTA.

The crystal structure of holo BoNTA includes two polypeptide chains that are linked by a disulfide bond. The light chain (50 KDa) is a zinc endopeptidase that specifically cleaves neuronal proteins responsible for acetylcholine release. The heavy chain (100 KDa) mediates selective binding to neuronal cells via specific gangliosides and translocates the light chain into the cytosol after receptor-mediated endocytosis of the entire molecule. Of eight serotypes of BoNT, serotypes A, D and E are closely related, according to sequence analysis using ClustalW.

SUMMARY

This disclosure provides materials and methods for detoxifying Botulinum neurotoxin, including BoNTA, BoNTD, and/or BoNTE. For example, small-molecule inhibitors of BoNTA are provided. A small-molecule inhibitor can inhibit the zinc protease, an endopeptidase, of BoNTA, BoNTD, and/or BoNTE. In some cases, a small-molecule inhibitor can inhibit the zinc protease of BoNTA. Methods for using such small-molecule inhibitors to treat, prevent, or ameliorate one or more symptoms of Botulinum poisoning or disorders associated with Botulinum poisoning, including food-borne botulism and BoNTA, BoNTD, and/or BoNTE poisoning, are also provided. Kits and articles of manufacture containing one or more small-molecule inhibitors and accessory items are also provided.

Accordingly, compositions comprising a compound according to Formula I, II, III, and IV, as described further herein, are provided. Methods of treating or ameliorating one or more symptoms associated with Botulinum toxin poisoning in a mammal comprising administering a composition comprising a compound according to Formula I, II, III, and IV, as described further herein, are also provided. In some embodiments, the composition comprises Compound 12. In other embodiments, the composition comprises Compound 30b. In yet other embodiments, the composition comprises Compound 30m. In some embodiments, the mammal is a human.

A method for treating or ameliorating one or more symptoms of Botulinum toxin poisoning can further comprise administering a trivalent equine antitoxin or penicillin G to said mammal.

In another aspect, a method for inhibiting a zinc protease activity is provided, comprising contacting a zinc protease with a compound according to Formula I, II, III, or IV.

In another aspect, a kit comprising a composition according to Formula I, II, III, or IV is also provided. The composition can be in the form of an injectable composition in the kit.

Also provided is a composition according to Formula I, II, III, or IV for use in the treatment or amelioration of Botulinum toxin poisoning, as well as the use of a composition according to Formula I, II, III, or IV in the preparation of a medicament for the treatment or amelioration of Botulinum toxin poisoning.

Articles of manufacture including a composition according to Formula I, II, III, or IV disposed within a pill, a tablet, a capsule, or a syringe are further provided.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 Chemical structures of inhibitors 1-14 and their inhibition on the zinc endopeptidase of botulinum neurotoxin serotype A at a drug concentration of 100 µM.

DETAILED DESCRIPTION

Figure 2:
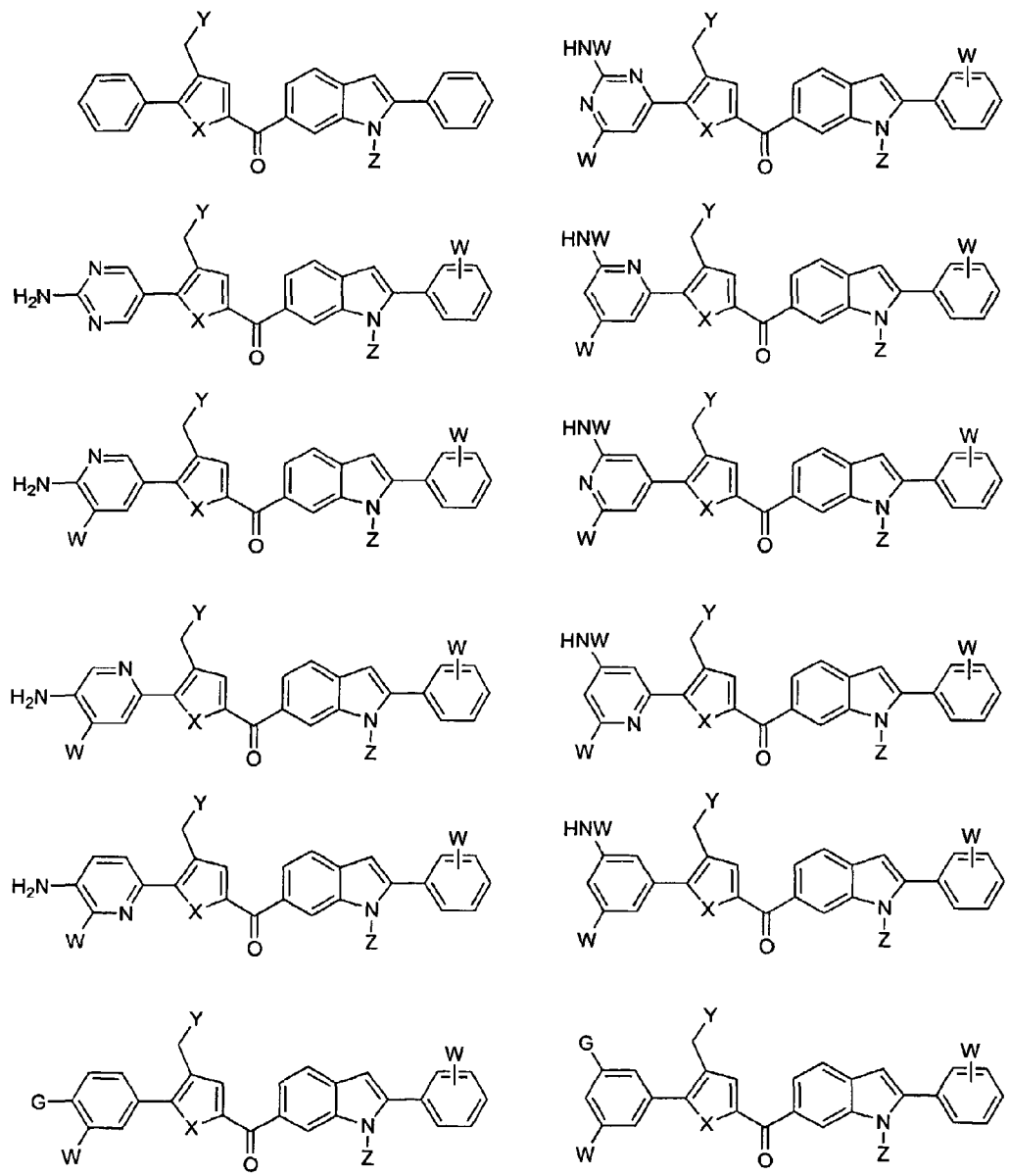
FIG. 2 sets forth various embodiments of Formula I, as described herein.

Provided herein are small-molecule inhibitors of Botulinum neurotoxin, including BoNTA, BoNTD and BoNTE. The small-molecule inhibitors were designed to inhibit the zinc protease (a zinc endopeptidase) of BoNTA using, in part, information obtained from molecular modeling studies of the endopeptidase and its active site. For example, the four-ligand coordination of the zinc ion embedded in the active site of the zinc endopeptidase was computationally simulated with the cationic dummy atom (CaDA) approach. (See Pang, Y. P. *J. Mol. Model.* 1999, 5, 196; Pang, Y. P.; Xu, K.; El Yazal, J.; Prendergast, F. G. *Protein Sci.* 2000, 9, 1857; Pang, Y.-P. *Proteins.* 2001, 45, 183; Oelschlaeger, P.; Schmid, R. D.; Pleiss, J. *Protein Eng.* 2003, 16, 341; and Oelschlaeger, P.; Schmid, R. D.; Pleiss, J. *Biochemistry* 2003, 42, 8945.) The CaDA approach enabled (i) refinement of the endopeptidase, (ii) identification of small molecules that were able to coordinate the zinc ion upon binding to the active site via docking and molecular dynamics simulations, and (iii) optimization of the zinc-coordinating molecules via free energy perturbation study (Pang, Y. P.; Miller, J. L.; Kollman, P. A. *J. Am. Chem. Soc.* 1999, 121, 1717).

A. DEFINITIONS

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of Botulinum neurotoxin poisoning, e.g., BoNTA poisoning, are ameliorated or otherwise beneficially altered. Treatment also encompasses any pharmaceutical use of the compositions herein, such as uses for treating diseases, disorders, or ailments in which Botulinum neurotoxin is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response in an assay that measures such response.

As used herein, the term $K_i$ represents the dissociation constant of an enzyme/inhibitor complex. It is theoretically independent of the substrate against which the inhibitor is tested. $K_i$ can be calculated from an $IC_{50}$ using the equation: $K_i = IC_{50} * K_m/(S+K_m)$, where S is the concentration of substrate, and $K_m$ is the substrate concentration (in the absence of inhibitor) at which the velocity of the reaction is half-maximal. The $K_i$ of an inhibitor for inhibition of a particular substrate (fixed $K_m$) is constant.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds provided herein may contain chiral centers. Such chiral centers may be of either the (R) or (S) configuration, or may be a mixture thereof. In certain cases, the (S) configuration may be preferred, e.g., at the 2-mercapto position of certain compounds described herein. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" refer to carbon chains that may be straight or branched. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl).

As used herein, "cycloalkyl" refers to a saturated mono- or multi-cyclic ring system, in certain embodiments of 3 to 10 carbon atoms, in other embodiments of 3 to 6 carbon atoms. The ring systems of the cycloalkyl groups may be composed of one ring or two or more rings which may be joined together in a fused, bridged or spiro-connected fashion. Examples include, but are not limited to, cyclopropyl, cyclobutyl, cyclopentyl, and cyclohexyl.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members, where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen.

As used herein, "carboxy" refers to a divalent radical, —C(O)O—.

As used herein, "aminocarbonyl" refers to —C(O)NH$_2$.

As used herein, "aminoalkyl" refers to —RNH$_2$, in which R is alkyl.

As used herein, "alkoxy" and "alkylthio" refer to RO— and RS—, in which R is alkyl.

As used herein, "aryloxy" and "arylthio" refer to RO— and RS—, in which R is aryl.

As used herein, "amido" refers to the divalent group —C(O)NH.

As used herein, "hydrazide" refers to the divalent group —C(O)NHNH—.

Where the number of any given substituent is not specified (e.g., haloalkyl), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. COMPOUNDS

The compounds provided herein exhibit in vitro activity against Botulinum neurotoxin poisoning (i.e., BoNTA, BoNTD, and/or BoNTE poisoning) and associated disorders. For example, the compounds provided herein can inhibit the zinc endopeptidase of BoNTA, which is thought to specifically cleave neuronal proteins that are responsible for acetylcholine release. In some embodiments, the inhibition of BoNTA is specific as compared to Botulinum neurotoxin serotype B (BoNTB). In one embodiment, the compounds treat, prevent, or ameliorate one or more symptoms associated with Botulinum neurotoxin poisoning, including BoNTA poisoning. In certain embodiments, the compounds inhibit the endopeptidase activity of BoNTA. In some embodiments, the compounds inhibit the endopeptidase activity of BoNTA, or BoNTE, or BoNTD.

Use of any of the compounds provided herein, or their pharmaceutically acceptable salts or derivatives, in the treatment or amelioration of Botulinum neurotoxin poisoning (e.g., BoNTA poisoning), or associated disorders is also provided, as well as use of any of the compounds, or pharmaceutically acceptable salts or derivatives, in the preparation of a medicament for the treatment or amelioration of Botulinum neurotoxin poisoning (e.g., BoNTA poisoning).

Compounds for use in the compositions and methods provided herein, or pharmaceutically acceptable salts or derivatives thereof, can have Formula I:

where:

$T_1$-$T_9$ have $sp^2$ hybridization;

$T_1$ is independently selected from C, N, O and S, where $T_{10}$ is either W if $T_1$ is C or N, or not present if $T_1$ is O or S;

$T_2$-$T_9$ are independently selected from C and N;

each W is selected, independently, from the group consisting of H; $NH_2$; OH; halo; alkyl, alkenyl, alkynyl, alkoxy, alkylthio, cycloalkyl, aryloxy, heteroaryl, heteroalkyl, and heterocyclyl groups having from 1 to 8 C atoms, provided that when W is attached to $X_1$, W is not present when $X_1$ is N;

each $X_1$ is selected, independently, from N and C;

$X_2$ is S, O, or NH;

G is selected from H; halo; $NH_2$; OH; NHR, NRR, S(R), R($NH_2$), R, and O(R), wherein each R is independently an alkyl group having from 1 to 6 carbon atoms, when the $X_1$ to which G is attached is C; or G is not present when the $X_1$ to which G is attached is N;

B is NHW or G when $X_1$ to which B is attached is C; or not present when $X_1$ to which B is attached is N;

Y is C(=O)NR'OH, $CO_2H$, imidazolyl, $SO_2NH_2$, R'$SO_2NH_2$, R'SH, or CONR'$NH_2$, wherein R' is H or an alkyl group having from 1 to 6 carbon atoms; and Z is selected from the group consisting of $(CH_2)_mA$, $(CH_2)_mNH(CH_2)_nA$, $CO(CH_2)_mA$, $CO(CH_2)_mNH(CH_2)_nA$, $SO_2(CH_2)_mA$, and $SO_2(CH_2)_mNH(CH_2)_nA$, wherein m and n can be, independently, an integer from 2 to 14, inclusive;

wherein A can be selected from the group consisting of amino, imidazolyl, piperidinyl, piperazinyl, morpholinyl, E1, E2, E3, and E4:

where $W_2$ can be selected from the group consisting of H, OH, N($R_1$)($R_2$), wherein $R_1$ and $R_2$ are, independently, H or alkyl having from 1 to 6 C atoms; and alkyl having from 1 to 6 C atoms.

In some embodiments, $T_8$ and $T_9$ are C.
In some embodiments, $T_1$-$T_2$ and $T_4$-$T_9$ are C.
In some embodiments, $T_3$ is N.
In some embodiments, $T_1$ is C and $T_{10}$ is H.
In some embodiments, W is H, OH, $NH_2$, or alkyl having from 1 to 4 C atoms.
In some embodiments, Y is C(=O)NHOH.
In some embodiments, $X_2$ is S.
In some embodiments, Z is $(CH_2)_mA$, where m is an integer from 1 to 6. In some embodiments, m is 4. In some embodiments, A is amino.

In certain embodiments, at least one of $X_1$ is N. In some embodiments, at least two of $X_1$ are N. In some embodiments, all $X_1$ are C.

In certain embodiments, $T_3$ is N and Z is $(CH_2)_4NH_2$. In some embodiments, $T_3$ is N, and $T_1$-$T_2$, $T_4$-$T_9$ are C.

In certain embodiments, G is selected from H, F, Cl, Br, $NH_2$, aminoalkyl groups having from 1 to 4 C atoms, OH, and alkylthio and alkoxy groups having from 1 to 4 C atoms.

Compounds of Formula I having the formulae as set forth in FIG. 2 are also provided, wherein B, G W, $X_1$, $X_2$, Y and Z are as provided above. In certain embodiments, any of the compounds 1-14 set forth in FIG. 1 can be used in the compositions and methods herein. For example, compound 12 can be used in a composition or method provided herein. In some cases, compound 13 can be used in a composition or method provided herein. In certain cases, compound 14 can be used in a composition or method provided herein.

Figure 8:
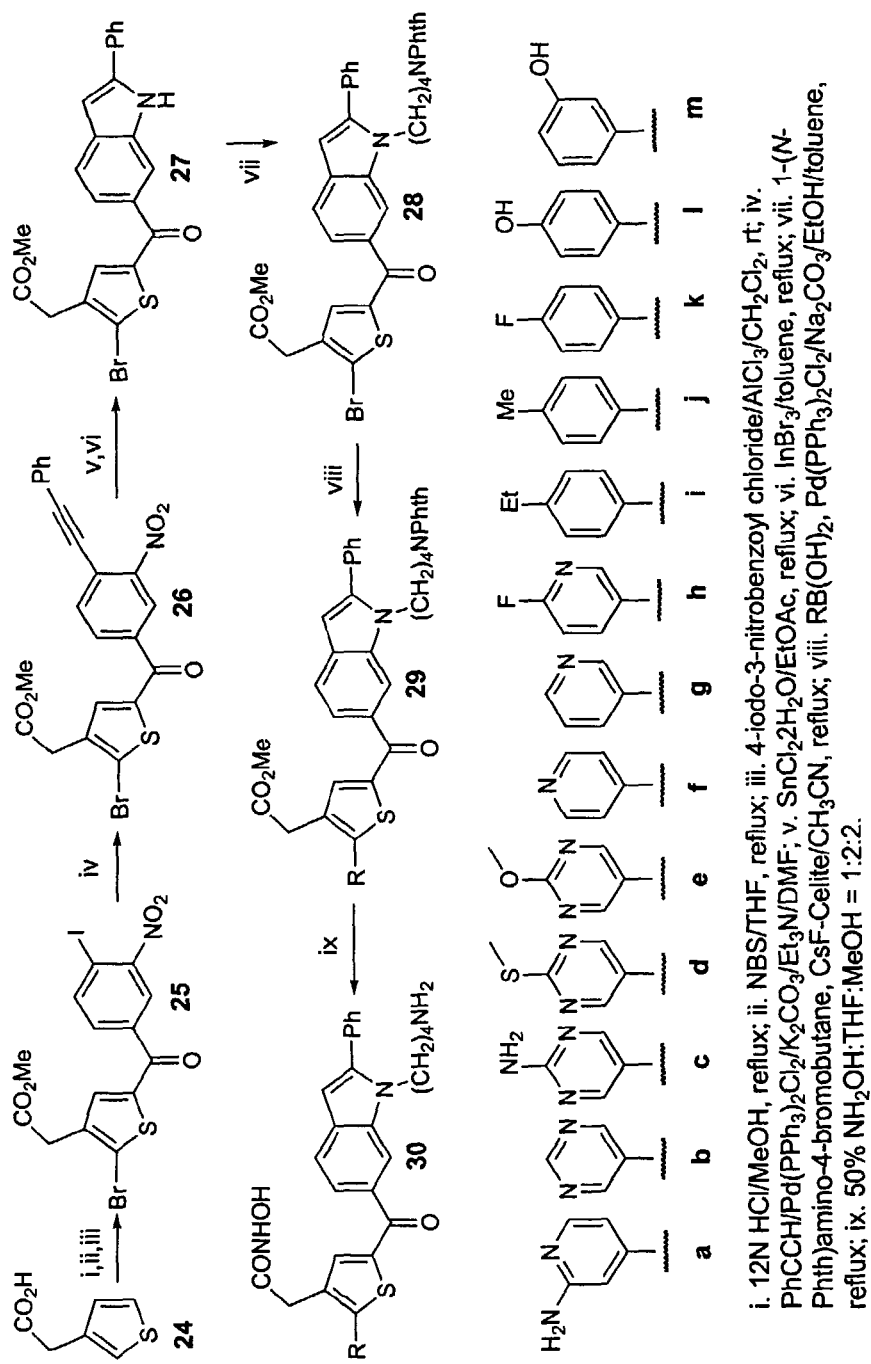
FIG. 8 is a synthetic scheme for the preparation of Compounds 30a-m. Compounds 30a-m represent various embodiments of Formula I, as described herein.

Compounds of Formula I having the formulae as set forth in FIG. 8 are also provided. In certain embodiments, any of the compounds set forth in FIG. 8 can be used in compositions and methods herein. In some embodiments, compounds 30a, 30b, 30k, or 30m can be used in the compositions and methods herein.

Compounds for use in the compositions and methods provided herein can have Formula II:

or a pharmaceutically acceptable salt or derivative thereof, wherein:

W is selected from the group consisting of H; alkyl, alkenyl, alkynyl, alkoxy and cycloalkyl groups having from 1 to 8 C atoms; aryloxy, heteroaryl, heteroalkyl, and heterocyclyl;

each $X_1$ is selected, independently, from N and C;

$X_2$ is S, O, or NH;

G is selected from H, halo, $NH_2$, OH, $R(NH_2)$, and O(R), wherein R is an alkyl group having from 1 to 6 carbon atoms;

B is NHW or G when $X_1$ to which it is attached is C; or not present when $X_1$ to which it is attached is N;

Y is $C(=O)N(R')OH$, $CO_2H$, imidazolyl, $SO_2NH_2$, $R'SO_2NH_2$, R'SH, or $C(=O)N(R')NH_2$, wherein R' is H or an alkyl group having from 1 to 6 carbon atoms, and Z is selected from the group consisting of $(CH_2)_mA$, $(CH_2)_mNH(CH_2)_nA$, $CO(CH_2)_mA$, $CO(CH_2)_mNH(CH_2)_nA$, $SO_2(CH_2)_mA$, and $SO_2(CH_2)_mNH(CH_2)_nA$, wherein m and n can be, independently, an integer from 2 to 14, inclusive;

wherein A can be selected from the group consisting of amino, imidazolyl, piperidinyl, piperazinyl, morpholinyl, E1, E2, E3, and E4:

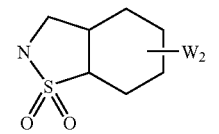

E1

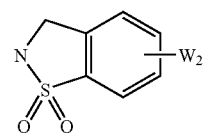

E2

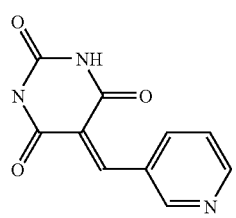

E3

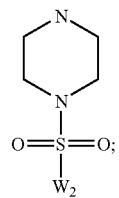

E4 where $W_2$ can be selected from the group consisting of H, OH, $N(R_1)(R_2)$, wherein $R_1$ and $R_2$ are, independently, H or alkyl having from 1 to 6 C atoms; and alkyl having from 1 to 6 C atoms.

In some embodiments, W is H or alkyl having from 1 to 4 C atoms.

In some embodiments, Y is $C(=O)NHOH$.

In some embodiments, $X_2$ is S.

In certain embodiments, Z is $(CH_2)_mA$, where m is an integer from 1 to 6.

In certain embodiments, A is amino.

In certain embodiments, at least one of $X_1$ is N.

In some embodiments, G is selected from H, F, Cl, Br, $NH_2$, aminoalkyl groups having from 1 to 4 C atoms, OH, and alkoxy groups having from 1 to 4 C atoms.

Figure 3:
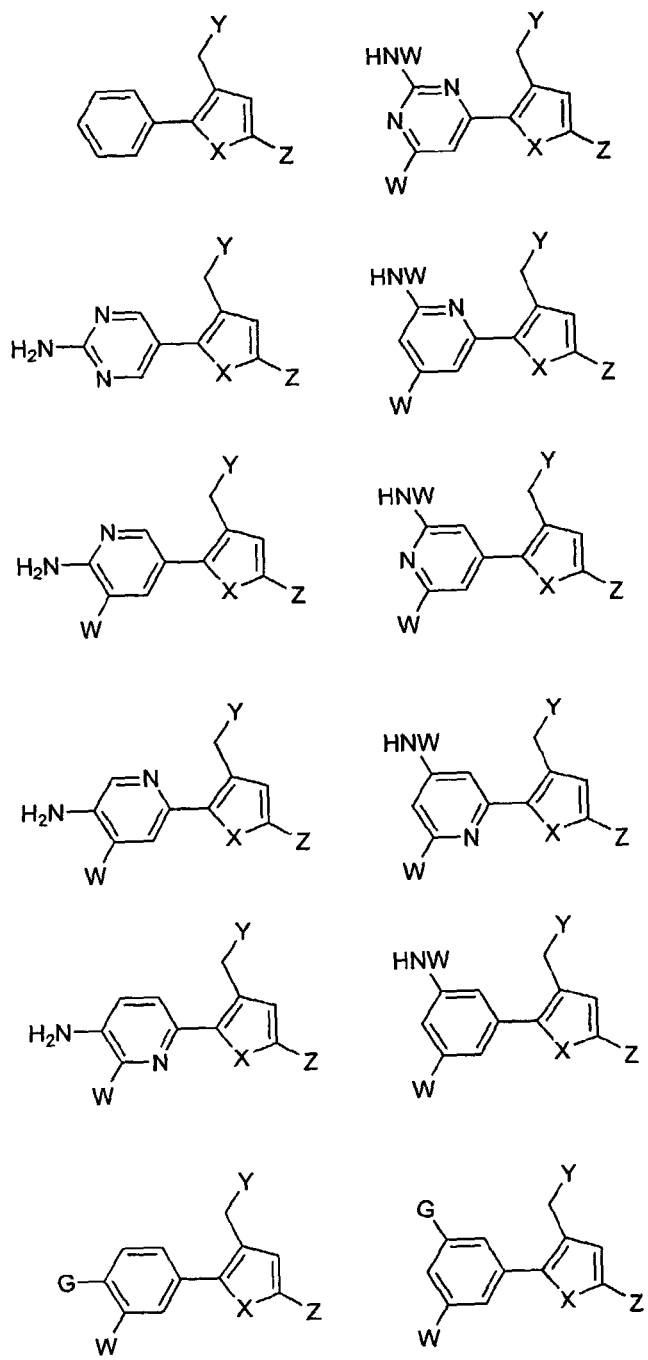
FIG. 3 sets forth various embodiments of Formula II, as described herein.

Compounds of Formula II can also have a formula as set forth in FIG. 3, where B, W, Y, $X_1$, $X_2$, Q and Z are as described above.

Compounds for use in the compositions and methods provided herein can have Formula III:

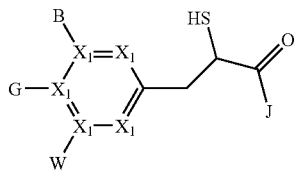

or a pharmaceutically acceptable salt or derivative thereof, wherein:

W is selected from the group consisting of H; alkyl, alkenyl, alkynyl, alkoxy and cycloalkyl groups having from 1 to 8 C atoms; aryloxy, heteroaryl, heteroalkyl, and heterocyclyl;

each $X_1$ is selected, independently, from N and C;

G is selected from H, halo, $NH_2$, OH, $R(NH_2)$, and O(R), wherein R is an alkyl group having from 1 to 6 carbon atoms;

B is NHW or G when $X_i$ to which it is attached is C; or not present when $X_1$ to which it is attached is N;

wherein at least one of B, G and W is not H;

J is selected from $-(CH_2)_mA$, $-(CH_2)_mNH(CH_2)_nA$, $-N(CH_2)_mA$, $-N(CH_2)_mNH(CH_2)_nA$, ArgAlaThrLysMetLeu (SEQ ID NO:1), HisAlaThrLysMetLeu (SEQ ID NO:2), homoHisAlaThrLysMetLeu (SEQ ID NO:3), homohomoHisAlaThrLysMetLeu (SEQ ID NO:4), homoPheAlaThrLysMetLeu (SEQ ID NO:5), homohomoPheAlaThrLysMetLeu (SEQ ID NO:6), homoTrpAlaThrLysMetLeu (SEQ ID NO:7), and homohomoTrpAlaThrLysMetLeu (SEQ ID NO:8);

wherein A is selected from the group consisting of amino, imidazolyl, piperidinyl, piperazinyl, morpholinyl, E1, E2, E3, and E4:

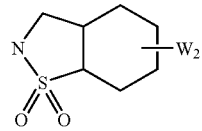

E1

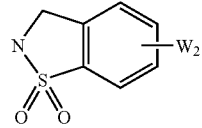

E2

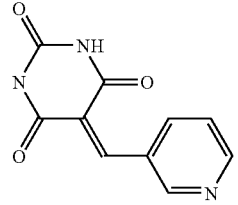

E3

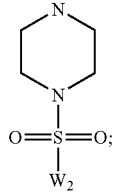

E4 where $W_2$ can be selected from the group consisting of H, OH, $N(R_1)(R_2)$, wherein $R_1$ and $R_2$ are, independently, H or alkyl having from 1 to 6 C atoms; and alkyl having from 1 to 6 C atoms.

In some embodiments, B, G, and W cannot each be H when each $X_1$ is selected to be C.

In some embodiments, at least one $X_1$ is N. In some embodiments, at least two $X_1$ are N.

In some embodiments, the composition has an S stereochemistry at the 2-mercapto group.

In some embodiments, W is H or alkyl having from 1 to 4 C atoms.

In some embodiments, G is selected from H, F, Cl, Br, $NH_2$, aminoalkyl groups having from 1 to 4 C atoms, OH, and alkoxy groups having from 1 to 4 C atoms.

In some embodiments, J is selected from SEQ ID NO:1, SEQ ID NO:2, SEQ ID NO:3, SEQ ID NO:4, SEQ ID NO:5, SEQ ID NO:6, SEQ ID NO:7, and SEQ ID NO:8. In certain cases, all of the amino acids of J are in the L-form. In some cases, the C-terminal amino acid of a J peptide selected from SEQ ID NO:1-SEQ ID NO:8 is amidated.

Figure 4:
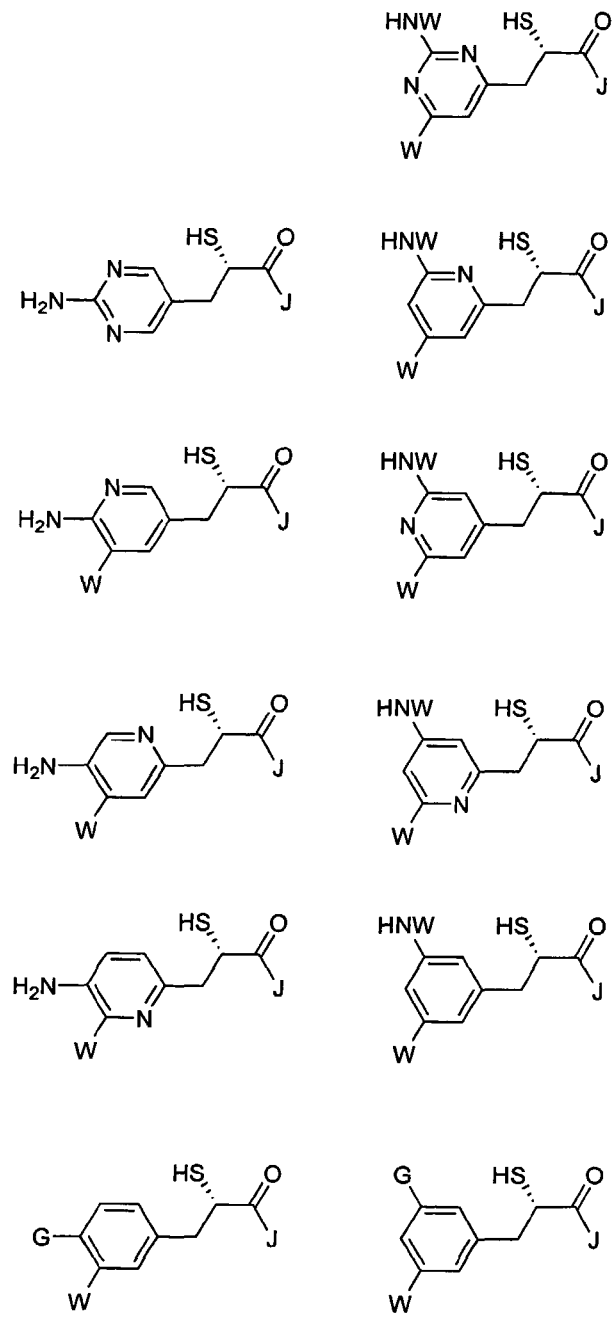
FIG. 4 sets forth various embodiments of Formula III, as described herein.

Compounds according to Formula III can also have a formula as set forth in FIG. 4, wherein B, G, W, $X_1$ and J are as defined above.

Compounds for use in the compositions and methods provided herein can have Formula IV:

or a pharmaceutically acceptable salt or derivative thereof, where:

each $X_1$ is selected, independently, from N and C; and where $J_2$ is selected from $—(CH_2)_mA$, $—(CH_2)_mNH(CH_2)_nA$, $—N(CH_2)_mA$, $—N(CH_2)_mNH(CH_2)_nA$, HisAlaThrLysMetLeu (SEQ ID NO:2), homoHisAlaThrLysMetLeu (SEQ ID NO:3), homohomoHisAlaThrLysMetLeu (SEQ ID NO:4), homoPheAlaThrLysMetLeu (SEQ ID NO:5), homohomoPheAlaThrLysMetLeu (SEQ ID NO:6), homoTrpAlaThrLysMetLeu (SEQ ID NO:7), and homohomoTrpAlaThrLysMetLeu (SEQ ID NO:8), where A is selected from the group consisting of amino, imidazolyl, piperidinyl, piperazinyl, morpholinyl, E1, E2, E3, and E4:

where $W_2$ can be selected from the group consisting of H, OH, $N(R_1)(R_2)$, wherein $R_1$ and $R_2$ are, independently, H or alkyl having from 1 to 6 C atoms; and alkyl having from 1 to 6 C atoms.

In some embodiments, $J_2$ is selected from SEQ ID NO:2, SEQ ID NO:3, SEQ ID NO:4, SEQ ID NO:5, SEQ ID NO:6, SEQ ID NO:7, and SEQ ID NO:8. In some embodiments, all amino acids are in their L form. In some embodiments, the sterochemistry of the mercapto-substituted carbon is S. In some cases, the C-terminal amino acid of a J peptide selected from SEQ ID NO:1-SEQ ID NO:8 is amidated.

It should be noted, with respect to Formula III and IV, that HomoHis and HomohomoHis are analogs of His in which the imidazole group is connected to the alpha carbon with ethylene and propylene, respectively. HomoPhe and HomohomoPhe are analogs of Phe in which the phenyl group is connected to the alpha carbon with ethylene and propylene, respectively. HomoTrp and HomohomoTrp are analogs of Trp in which the indole is connected to the alpha carbon with ethylene and propylene, respectively.

C. PREPARATION OF THE COMPOUNDS

The compounds for use in the compositions and methods provided herein may be obtained from commercial sources (e.g., Aldrich Chemical Co., Milwaukee, Wis.), or may be prepared by methods well known to those of skill in the art or by the methods shown herein (e.g., see FIGS. 5-8 and the Examples, below). One of skill in the art would be able to prepare all of the compounds for use herein by routine modification of these methods using the appropriate starting materials.

D. FORMULATION OF PHARMACEUTICAL COMPOSITIONS

The pharmaceutical compositions provided herein contain therapeutically effective amounts of one or more of the compounds provided herein that are useful in the treatment, prevention, or amelioration of one or more of the symptoms associated with Botulinum toxin poisoning (e.g., BoNTA poisoning), or a disorder or ailment in which Botulinum toxin poisoning (e.g., BoNTA poisoning) is implicated, and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats or ameliorates one or more of the symptoms of Botulinum toxin poisoning, e.g., BoNTA poisoning.

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disorder being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, or in one embodiment 0.1-95%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action. The active ingredient is a compound or pharmaceutically acceptable derivative thereof as described herein. Higher concentrations, up to about 98% by weight of the active ingredient, may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

2. Injectables, Solutions, and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration should be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture (e.g., kits) containing packaging material, a compound or pharmaceutically acceptable derivative thereof provided herein within the packaging material, and a label that indicates that the compound or composition, or pharmaceutically acceptable derivative thereof, is useful for treatment, prevention, or amelioration of one or more symptoms or disorders in which Botulinum neurotoxin poisoning, including BoNTA poisoning, is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

8. Sustained Release Formulations

Also provided are sustained release formulations to deliver the compounds to the desired target at high circulating levels (between $10^{-9}$ and $10^{-4}$ M). The levels are either circulating in the patient systemically, or in one embodiment, localized to a site of, e.g., paralysis.

It is understood that the compound levels are maintained over a certain period of time as is desired and can be easily determined by one skilled in the art. Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, in one embodiment 20 to 25%, and the amount of coating will be from 10 to 25% of the weight of the active material, and in another embodiment, 15 to 20% of the weight of active material. Any conventional pharmaceutically acceptable plasticizer may be incorporated into the coating.

The compounds provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

E. EVALUATION OF THE ACTIVITY OF THE COMPOUNDS

The activity of the compounds provided herein as inhibitors of Botulinum toxin poisoning (e.g., BoNTA poisoning), or BoNTA zinc endopeptidase activity, may be measured in standard assays, e.g., HPLC assays, such as those described in Schmidt, J. J., Bostian, K. A., J. Protein Chem. (1997), 16, 19, in which a test compound was added to an assay mixture containing a substrate of Botulinum toxin, followed by addition of the toxin. The assay time and toxin concentration were adjusted so that less than 10% of the substrate was hydrolyzed. The assay was stopped by acidification with trifluoroacetic acid and analyzed by reverse-phase HPLC. The percent proteolysis of the substrate was calculated by dividing the combined areas of the peaks representing the cleavage products by the sum of the areas of the cleavage products plus uncleaved parent substrate.

F. METHODS OF USE OF THE COMPOUNDS AND COMPOSITIONS

Provided herein are methods to treat, prevent, or ameliorate symptoms or disorders associated with Botulinum toxin poisoning, including food-borne botulism and BoNTA, BoNTD or BoNTE poisoning; and methods to inhibit zinc protease activity, including BoNTA, BoNTD or BoNTE zinc protease activity. The methods include administering one or more of the compounds described herein, or a pharmaceutically acceptable salt or derivative thereof, to a mammal, e.g., a human, cat, dog, horse, pig, cow, sheep, mouse, rat, or monkey. In certain cases, the methods can be used to counter-effect Botulinum toxin poisoning from cosmetic Botox injections. In certain cases, the methods can be used to counter-effect Botulinum toxin poisoning from biological-based weapons.

In certain embodiments, the symptoms or disorders associated with Botulinum toxin poisoning include one or more of the following: muscular paralysis, difficulty breathing, asphyxiation, suffocation, fatigue, dizziness, double vision, blurred vision, dysphagia, dry mouth, dysarthria, sore throat, dyspnea, constipation, nausea, vomiting, abdominal pain, diarrhea, arm weakness, leg weakness, paresthesia, alert mental status, ptosis, gaze paralysis, fixation or dilation of the pupils, nystagmus, facial palsy, diminished gag reflex, and tongue weakness.

In practicing the methods, effective amounts of the compounds or composition provided herein are administered. Such amounts are sufficient to achieve a therapeutically effective concentration of the compound or active component of the composition in vivo.

EXAMPLES

Materials and Methods

1. Preparation of the Zinc- and Inhibitor-Bound Endopeptidase Models

A truncated endopeptidase (residues 1-429, 453-471, and 497-544) was used in the study. The initial 3D structure of the truncated zinc-containing endopeptidase was taken from an available crystal structure of BoNTA (PDB code: 3BTA) (Lacy, D. B.; Tepp, W.; Cohen, A. C.; Dasgupta, B. R.; Stevens, R. C. Nat. Struct. Biol. 1998, 5, 898) and modified according to a published procedure (Pang, Y. P.; Xu, K.; El Yazal, J.; Prendergast, F. G. Protein Sci. 2000, 9, 1857). The zinc divalent cation in the crystal structure was replaced by the tetrahedron-shaped zinc divalent cation that has four cationic dummy atoms surrounding the central zinc ion (Pang, Y. P. J. Mol. Model. 1999, 5, 196). The first-shell zinc coordinates (His222 and His226; and Glu261) were deprotonated as histidinate and glutamate, respectively (El Yazal, J.; Pang, Y. P. J. Phys. Chem. B 1999, 103, 8773; El Yazal, J.; Roe, R. R.; Pang, Y. P. J. Phys. Chem. B 2000, 104, 6662; El Yazal, J.; Pang, Y. P. J. Mol. Struct., (Theochem) 2001, 545, 271.) Glu260 and Glu350, which form a hydrogen bond with His222 and His 226 respectively, were protonated as glutamic acid. All other His residues were protonated as histidinium. Inhibitor 12 was manually docked into the active site according to the 1-bound endopeptidase complex generated by the EUDOC program (Pang, Y. P.; Perola, E.; Xu, K.; Prendergast, F. G. J. Comp. Chem. 2001, 22, 1750). Four sodium ions were added to the surface of the protein to neutralize the protein. The published force field parameters of the tetrahedron-shaped zinc divalent cation (Pang, Y.-P. Proteins. 2001, 45, 183) were used in energy minimizations and in the following described molecular dynamics simulations, with the exception that the force constants for DZ-DZ and ZN-DZ bonds were changed from 540 to 640 kcal/mol. The RESP charges and force field parameters of inhibitor 12 were generated by the ANTECHAMBER module of AMBER 7 program (Pearlman, D. A.; Case, D. A.; Caldwell, J. W.; Ross, W. S.; Cheatham III, T. E. Comput. Phys. Commun. 1995, 91, 1) using the structure of 12 optimized at the HF/6-31 G* level by the Gaussian 98 Program (Frisch, M. J.; Trucks, G. W.; Schlegel, H. B.; Scuseria, G. E.; Robb, M. A.; Gaussian, Inc.: Pittsburgh Pa., 2003). A 10,000-step energy minimization was first performed on inhibitor 12 with a positional constraint applied to the rest of the complex. A 50-step energy minimization was then performed on the tetrahedron-shaped zinc divalent cation and 12 with a positional constraint applied to the endopeptidase only. A 100-step energy minimization was lastly performed on the entire complex without any restraints or constraints.

2. Virtual Screening

Computational screening of an in-house database of 2.5 million chemical structures for inhibitor leads of BoNTA was carried out according to a published protocol (Perola, E.; Xu, K.; Kollmeyer, T. M.; Kaufmann, S. H.; Prendergast, F. G. *J. Med. Chem.* 2000, 43, 401). In this study the EUDOC program (Pang, Y. P.; Perola, E.; Xu, K.; Prendergast, F. G. *J. Comp. Chem.* 2001, 22, 1750) was used on a dedicated terascale computer with 420 Intel Xeon processors (2.2 GHz). A docking box (3.5×3.5×8.0 $Å^3$) was defined in the active site of the zinc-bound endopeptidase that was modified from the crystal structure of BoNTA (PDB code: 3BTA) using the procedure described above. The active-site residues that surrounded the docking box were Ile160, Phe162, Phe193, Thr214, Thr219, His222, Glu223, Arg362, Tyr365, Asp369, and Zn(II). The translational and rotational increments for the screening were set at 1.0 Å and 10° of arc, respectively.

3. Multiple Molecular Dynamics Simulations

The multiple molecular dynamics simulations (MMDSs) were performed according to a published protocol (Pang, Y.-P. *Proteins.* 2004, 57, 747; Pang, Y.-P. *Proteins* 2001, 45, 183) using the parallel PMEMD module of the AMBER8 program (Pearlman, D. A.; Case, D. A.; Caldwell, J. W.; Ross, W. S.; Cheatham III, T. E. *Comput. Phys. Commun.* 1995, 91, 1) with the Cornell et al. force field (parm96.dat) (Cornell, W. D.; Cieplak, P.; Bayl), C. I.; Gould, I. R.; Merz Jr., K. M. *J. Am. Chem. Soc.* 1995, 117, 5179). The zinc- and 12-containing endopeptidase complex was solvated with 14,972 TIP3P water molecules (Jorgensen, W. L.; Chandreskhar, J.; Madura, J. D.; Impey, R. W.; Klein, M. L. *J. Chem. Phys.* 1982, 79, 926) and neutralized with four sodium ions, resulting in a system of 52,993 atoms. The topology and coordinate files of the zinc- and 12-containing endopeptidase were generated by the LINK, EDIT, and PARM modules of the AMBERS program (Pearlman, D. A.; Case, D. A.; Caldwell, J. W.; Ross, W. S.; Cheatham III, T. E. *Comput. Phys. Commun.* 1995, 91, 1). All simulations used (1) a dielectric constant of 1.0, (2) the Berendsen coupling algorithm (Berendsen, H. J. C.; Postma, J. P. M.; van Gunsteren, W. F.; Di Nola, A.; Haak, J. R. *J. Chem. Phys.* 1984, 81, 3684), (3) a periodic boundary condition at a constant temperature of 300 K and a constant pressure of 1 atm with isotropic molecule-based scaling, (4) the Particle Mesh Ewald method to calculate long-range electrostatic interactions (Darden, T. A.; York, D. M.; Pedersen, L. G. *J. Chem. Phys.* 1993, 98, 10089), (5) iwrap=1 to generate the trajectories for interaction energy calculations using the EUDOC program (Pang, Y. P.; Perola, E.; Xu, K.; Prendergast, F. G. *J. Comp. Chem.* 2001, 22, 1750), (6) a time step of 1.0 fs, (7) the SHAKE-bond-length constraints applied to all bonds involving the hydrogen atom (Miyamoto, S.; Kollman, P. A. *J. Comp. Chem.* 1992, 13, 952), and (8) default values of all other inputs of the PMEMD module.

4. Synthesis

Melting points are uncorrected. Infrared spectra were recorded on a Thermo Nicolet Avatar 370 FT-IR. $^1$H NMR spectra were recorded on Bruker Avance 500 (500 MHz), Bruker Avance 600 (600 MHz), or Varian Mercury 400 (400 MHz), or Varian AM60 (60 MHz) spectrometers. $^{13}$C NMR spectra were recorded on Bruker Avance 500 (125 MHz), Bruker Avance 600 (150 MHz), or Varian Mercury 400 (100 MHz) spectrometers. Chemical shifts are reported in ppm from the solvent resonance as the internal standard. Data are reported as follows: chemical shift, multiplicity (s=single, d=doublet, t=triplet, q=quartet, p=pentet, br=broad, m=multiplet), coupling constants (Hz), integration, and assignment. Mass Spectra were obtained on an HP5973 mass-selective detector with an SIS DIP-MS. Anhydrous THF and $CH_2Cl_2$ were obtained through activated alumina columns by the Solv-Tech Inc. Anhydrous DMF and $CH_3CN$ were obtained by distillation from $CaH_2$ under $N_2$. $POCl_3$ was distilled under $N_2$ immediately before use. All other commercially obtained reagents were used as received. Flash chromatography was performed on silica gel 60 (EM Science, 230-400 mesh).

(2-Phenylthiophene-3-yl)acetic acid methyl ester (15)

To a solution of 15.5 mL (3 eq) of freshly distilled DMF in a flame-dried flask at 5° C. was added 15.5 mL (2.5 eq) of freshly distilled $POCl_3$ under $N_2$. The $POCl_3$ mixture was warmed to room temperature followed by adding 13.75 g (66.66 mmol) of ethyl 3-benzoylpropionate (17). The resulting mixture was stirred at 80° C. for 16 h, cooled to room temperature, poured onto ice, and basified to pH=6 with solid NaOAc. The organic phase was extracted with EtOAc, washed with a saturated $NaHCO_3$ solution, dried over $MgSO_4$, filtered, and concentrated in vacuo. Kugelrohr distillation (195-200° C./0.1 mmHg) of the concentrated residue gave 14.84 g (88%) of 16 as a brown oil. The product consisted of E and Z isomers at a ratio of 2:1 was subjected to the next reaction without separation.

To a solution of 50 mL THF was added 5.00 g of 16 (19.79 mmol) followed by adding 2.06 mL (29.68 mmol) of mercaptoacetic acid and 8.27 mL of $NEt_3$ (59.36 mmol). The resulting solution was refluxed for 4 h. After the removal of THF by distillation, the residue was dissolved in 50 mL of DMF and the resulting solution was heated at 130° C. for 18 h. After DMF was removed in vacuo, the residue was diluted with 50 mL of $H_2O$ and extracted with EtOAc. The organic layer was dried over $MgSO_4$, filtered, and concentrated in vacuo. The residue was purified by flash chromatography (EtOAc/Hex 1:4) to give 2.71 g (56%) of (2-phenylthiophene-3-yl)acetic acid ethyl ester as a brown oil: $^1$H NMR (500 MHz, $CDCl_3$) δ 7.47 (d, J=7.5 Hz, 2H), 7.42 (d, J=7.4 Hz, 2H), 7.34 (t, J=7.4 Hz, 1H), 7.25 (d, J=5.2 Hz, 1H), 7.08 (d, J=5.2 Hz, 1H), 4.15 (q, J=7.1 Hz, 2H), 3.64 (s, 2H), 1.24 (t, J=7.1 Hz, 3H); $^{13}$C NMR (125 MHz, $CDCl_3$) δ 171.2, 140.6, 133.8, 129.7, 129.4, 128.5, 127.7, 124.0, 60.8, 34.5, 14.1.

To a solution of 4.34 g (17.63 mmol) of the above ethyl ester in 50 mL of MeOH was added 1.48 g (26.44 mmol) KOH. The resulting mixture was refluxed for 3 h. Afterward brown precipitates from the mixture were removed by filtration and the filtrate was concentrated in vacuo. The residue was dissolved in 20 mL of $H_2O$, washed with 20 mL of EtOAc, and acidified to pH~2-3 with 1N HCl. The resulting mixture was extracted with 30 mL of EtOAc and the organic phase was dried over $MgSO_4$, filtered, and concentrated in vacuo. The residue was dissolved in 50 mL of MeOH followed by adding 1.5 mL of concentrated HCl. The resulting solution was refluxed for 5 h. The solvent was removed in vacuo, and the residue was diluted with 20 mL of $H_2O$, neutralized with a saturated $NaHCO_3$ solution, and extracted with 30 mL of $CH_2Cl_2$. The organic layer was dried over $MgSO_4$, filtered, and concentrated in vacuo. The residue was purified by flash chromatography (EtOAc/Hex 1:4) to give 3.30 g (80%) of 15 as a white solid: mp 29-31° C.; $^1$H NMR (400 MHz, $CDCl_3$) δ 7.48-7.33 (m, 5H), 7.27 (d, J=5.2 Hz, 1H), 7.07 (d, J=5.2 Hz, 1H), 3.70 (s, 3H), 3.66 (s, 2H); $^{13}$C NMR (100 MHz, CDCl$_3$) δ 171.8, 140.7, 133.7, 129.7, 129.4, 129.2, 128.6, 127.8, 124.2, 52.1, 34.2; IR (KBr) cm$^{-1}$ 3113, 2941, 1728.

[5-(4-Chlorobenzoyl)-2-phenylthiophene-3-yl]acetic acid (1)

To a stirred solution of 0.05 g (0.22 mmol) of 15 and 27 uL (0.22 mmol) of 4-chlorobenzoyl chloride in 5 mL of dry CH$_2$Cl$_2$ was added 15 mg (0.11 mmol) of AlCl$_3$ in three portions at room temperature. The resulting mixture was stirred overnight. The reaction mixture was slowly poured onto 5 g of ice and allowed to warm to room temperature. The organic layer was dried over MgSO$_4$, filtered, and concentrated in vacuo. The residue was purified by flash chromatography (EtOAc/Hex 1:9) to give 0.04 g (50%) of [5-(4-chlorobenzoyl)-2-phenylthiophene-3-yl]acetic acid methyl ester as a white solid: $^1$H NMR (600 MHz, CDCl$_3$) δ 7.84 (d, J=8.2 Hz, 2H), 7.61 (s, 1H), 7.50-7.43 (m, 3H), 3.71 (s, 3H), 3.67 (s, 2H); $^{13}$C NMR (150 MHz, CDCl$_3$) δ 186.5, 171.1, 150.1, 140.8, 138.6, 137.3, 136.2, 132.6, 130.5, 129.2, 128.9, 128.8, 128.7, 52.2, 34.1; IR (KBr) cm$^{-1}$ 2949, 1737, 1623; LREIMS C$_{20}$H$_{15}$ClO$_3$S requires 370.04. Found: 370 ([M$^+$], 100%), 310 (40%), 139 (59%).

To a stirred solution of 0.15 g (0.40 mmol) of the above ester in a mixture of 2 mL of THF and 1 mL of H$_2$O was added 0.60 mL (0.60 mmol) of 1 N NaOH at room temperature. The resulting mixture was refluxed for 3 h. The solvent was evaporated in vacuo. The residue was dissolved in 5 mL of H$_2$O and acidified with 0.11 mL of 1N HCl to give 0.14 g (100%) of 1 as a pale yellow solid: mp 142-143° C.; $^1$H NMR (400 MHz, CDCl$_3$) δ 9.75 (brs, 1H), 7.84 (d, J=8.6 Hz, 2H), 7.62 (s, 1H), 7.462 (d, J=8.6 Hz, 2H), 7.46 (m, 5H), 3.71 (s, 2H); $^{13}$C NMR (100 MHz, CDCl$_3$) δ 186.6, 176.5, 150.6, 140.9, 138.8, 137.2, 136.1, 132.4, 130.6, 129.7, 129.3, 129.2, 129.1, 128.9, 34.0; IR (KBr) cm$^{-1}$ 3058, 2921, 1715, 1628; LREIMS C$_{19}$H$_{13}$ClO$_3$S requires 356.03. Found: 355 ([M$^+$], 100%), 310 (25%), 244 (25%), 139 (42%).

[5-(4-Bromobenzoyl)-2-phenylthiophene-3-yl]acetic acid (18)

Compound 18 was obtained in 74% yield using 4-bromobenzoyl chloride (from 4-bromobenzoic acid and SOCl$_2$) according to the same procedure as the one used for making 1. Methyl ester of 19: $^1$H NMR (60 MHz, CDCl$_3$) δ 7.71 (m, 4H), 7.61 (s, 1H), 7.47 (m, 5H), 3.71 (s, 3H), 3.67 (s, 2H); LREIMS C$_{20}$H$_{15}$BrO$_3$S requires 413.99. Found: 412 ([M-1$^+$], 100%), 413 (80%). 19 as a pale yellow solid: mp 147-150° C.; $^1$H NMR (400 MHz, CDCl$_3$) δ 7.77 (d, J=8.2 Hz, 2H), 7.66 (d, J=8.2 Hz, 2H), 7.62 (s, 1H), 7.48 (m, 5H), 3.72 (s, 2H); $^{13}$C NMR (100 MHz, CDCl$_3$) δ 186.8, 175.5, 150.6, 140.9, 137.3, 136.6, 132.5, 131.8, 130.7, 129.8, 129.3, 129.2, 129.1, 127.4, 33.9; IR (KBr) cm$^{-1}$ 2932, 1714, 1625; LREIMS C$_{19}$H$_{13}$BrO$_3$S requires 399.98. Found: 400 ([M$^+$], 100%).

2-[5-(4-Chlorobenzoyl)-2-phenylthiophene-3-yl]-N-hydroxyacetamide (2)

To a stirred mixture of 30 mg (0.08 mmol) of 1, 11 mg (0.08 mmol) of N-hydroxybenzotriazole (HOBt), 21 mg (0.11 mmol) of 1-ethyl-3-(3'-dimethylaminopropyl)carbodiimide hydrochloride (EDCI.HCl), and 28 mL (0.25 mmol) of 4-methylmorpholine in 5 mL dry CH$_2$Cl$_2$ was added 6 mg (0.08 mmol) of HONH$_2$.HCl at room temperature. The resulting mixture was stirred overnight and washed with 5 mL of H$_2$O. The organic layer was dried over MgSO$_4$, filtered, and concentrated in vacuo. The residue was purified by flash chromatography (EtOAc) to give 6 mg (20%) of 2 as a white viscous residue that solidified slowly at room temperature: $^1$H NMR (400 MHz, DMSO-d$_6$) δ 10.69 (s, 1H), 8.90 (brs, 1H), 7.86 (d, J=8.6 Hz, 2H), 7.72 (s, 1H), 7.68-7.50 (m, 7H), 3.39 (s, 2H); $^{13}$C NMR (100 MHz, DMSO-d$_6$) δ 185.9, 166.3, 148.8, 139.7, 138.6, 137.4, 136.0, 133.0, 132.3, 130.6, 129.2, 129.2, 129.1, 128.9; IR (KBr) cm$^{-1}$ 3305, 3223, 3060, 2921, 1746, 1631, 1436; LREIMS C$_{19}$H$_{14}$ClNO$_3$S requires 371.04. Found: 371 ([M$^+$], 9%), 355 (100%).

[5-(4-Iodo-3-nitrobenzoyl)-2-phenylthiophene-3-yl] acetic acid (19)

To 3.00 g (10.24 mmol) of 4-iodo-3-nitrobenzoic acid was added 20 mL of SOCl$_2$. The resulting solution was refluxed for 2 h. The excess thionyl chloride was removed by distillation. A residual amount of thionyl chloride was removed by N$_2$ stream and thereafter by high vacuum manifold (0.2 mmHg). The resulting acid chloride was dissolved in 30 mL of dry CH$_2$Cl$_2$, followed by adding 2.38 g (10.24 mmol) of 15. To the resulting mixture was added 5.46 g (40.95 mmol, 4.0 eq) of AlCl$_3$ in 5 portions at room temperature. The reaction was monitored by TLC. The completed reaction was quenched by pouring the reaction mixture onto 50 g of ice. The aqueous phase was extracted with 50 mL of CH$_2$Cl$_2$. The organic layer was dried over MgSO$_4$, filtered, and concentrated in vacuo. The residue was purified by flash chromatography (EtOAc/Hex 1:4) to give 3.86 g (74%) of 21 as a yellow solid: $^1$H NMR (500 MHz, CDCl$_3$) δ 8.34 (d, J=1.9 Hz, 1H), 8.23 (d, J=8.1 Hz, 1H), 7.76 (dd, J=1.9, 8.1 Hz, 1H), 7.64 (s, 1H), 7.48 (m, 5H), 3.73 (s, 3H), 3.69 (s, 2H); $^{13}$C NMR (125 MHz, CDCl$_3$) δ 184.3, 170.9, 152.9, 151.4, 142.5, 139.7, 138.8, 137.8, 132.9, 132.3, 131.0, 129.3, 129.2, 129.0, 125.6, 91.1, 52.3, 34.1.

Saponification of 21 using a stoichiometric amount of 1 N NaOH in a 1:1 mixture of MeOH and THF gave 19 as a yellow solid: mp 100-103° C.; $^1$H NMR (400 MHz, DMSO-d$_6$) δ 12.52 (brs, 1H), 7.75 (d, J=8.2 Hz, 1H), 7.72 (s, 1H), 7.52 (m, 5H), 7.21 (d, J=1.6 Hz, 1H), 6.78 (dd, J=1.6, 8.2 Hz, 1H), 3.66 (s, 2H); $^{13}$C NMR (100 MHz, DMSO-d$_6$) δ 186.7, 171.9, 148.8, 148.4, 139.9, 138.9, 138.6, 138.1, 132.4, 132.3, 129.2, 129.1, 128.7, 117.9, 113.7, 88.5, 34.0; IR (KBr) cm$^{-1}$ 3445, 3357, 2920, 1718, 1694; LREIMS C$_{19}$H$_{12}$INO$_5$S requires 492.95. Found: 492 ([M$^+$], 100%).

[5-(3-tert-Butoxycarbonylamino-4-iodobenzoyl)-2-phenylthiophene-3-yl]acetic acid (20)

To a solution of 5.54 g (10.92 mmol) of 21 in 100 mL EtOAc was added 12.32 g (54.60 mmol, 5.0 eq) of stannous chloride dihydrate. The resulting mixture was refluxed for 30 min under N$_2$, afterward quenched by pouring onto 100 g of ice, and basified to pH=8 with a saturated NaHCO$_3$ solution. The white milky mixture was filtered through a Celite pad to remove the tin oxides. The organic layer was dried over MgSO$_4$, filtered, and concentrated in vacuo to give 5.02 g (96%) of 22 as a yellow solid: $^1$H NMR (400 MHz, CDCl$_3$) δ 7.79 (d, J=8.2 Hz, 1H), 7.64 (s, 1H), 7.45 (m, 5H), 7.22 (d, J=1.5 Hz, 1H), 6.97 (dd, J=1.5, 8.2 Hz, 1H), 4.33 (brs, 2H), 3.72 (s, 3H), 3.68 (s, 2H); $^{13}$C NMR (100 MHz, CDCl$_3$) δ 187.7, 171.5, 150.3, 147.4, 141.2, 139.3, 137.7, 132.9, 130.7, 129.5, 129.3, 129.2, 120.4, 114.6, 89.2, 52.6, 34.4; IR (KBr) cm$^{-1}$ 3457, 3358, 1734, 1626; LREIMS C$_{20}$H$_{16}$INO$_3$S requires 476.99. Found: 477 ([M$^+$], 100%).

To a solution of 0.25 g (0.53 mmol) of 22 in 5 mL of dry THF was added sequentially 0.07 g (0.05 mmol) of DMAP, 0.26 g (1.19 mmol) of (Boc)$_2$O, and 0.37 mL (2.21 mmol) of DIEA. The resulting solution was stirred at room temperature for 12 h and afterward concentrated in vacuo. The residue was dissolved in a mixture of 2 mL of MeOH and 2 mL of THF. To the mixture was added 0.1 mL (1.0 mmol) of 1 N NaOH solution. The resulting solution was stirred at room temperature for 3 h. Afterward the color changed from orange to deep red. After the solvent was removed in vacuo, the residue was dissolved in 10 mL of EtOAc and washed with 10 mL of a saturated NH$_4$Cl solution. The organic layer was dried over MgSO$_4$, filtered, and concentrated in vacuo. The residue was purified by flash chromatography (EtOAc:Hex 1:1) to give 0.26 g (86%) of 20: $^1$H NMR (400 MHz, CDCl$_3$) δ 8.57 (d, J=2.2 Hz, 1H), 7.90 (d, J=8.2 Hz, 1H), 7.71 (s, 1H), 7.49 (m, 5H), 7.26 (dd, J=2.2, 8.2 Hz, 1H), 6.95 (s, 1H), 3.69 (s, 2H), 1.52 (s, 9H); $^{13}$C NMR (100 MHz, CDCl$_3$) δ, 186.7, 176.1, 152.4, 150.6, 140.9, 139.1, 139.0, 138.6, 137.8, 132.6, 129.9, 129.2, 129.0, 128.9, 124.6, 120.5, 81.6, 34.4, 28.2; IR (KBr) cm$^{-1}$ 3387, 2978, 1723.

Solid-Phase Synthesis of 3-7

Kaiser Oxime PS resin (purchased from Senn Chemicals, Switzerland, 1% DVB, 100-200 mesh, 1.6 mmol/g) packed in a Macro Kan (from IRORI Inc., San Diego, Calif.) was loaded with 18-20 according to a literature procedure (Thouin, E.; Lubell, W. D. *Tetrahedron Lett.* 2000, 41, 457), followed by cleavage with hydroxylamine to make 3, 4, and 5 or with hydrazine to make 6 and 7.

2-[5-(4-Bromobenzoyl)-2-phenylthiophene-3-yl]-N-hydroxyacetamide (3)

$^1$H NMR (400 MHz, DMSO-d$_6$) δ 10.68 (s, 1H), 8.89 (s, 1H), 7.81 (d, J=8.6 Hz, 2H), 7.78 (d, J=8.6 Hz, 2H), 7.72 (s, 1H), 7.67 (dd, J=1.4, 8.1 Hz, 2H), 7.54-7.47 (m, 3H), 3.69 (s, 2H); $^{13}$C NMR (100 MHz, DMSO-d$_6$) δ 186.1, 166.3, 148.9, 139.6, 138.6, 136.4, 133.0, 132.3, 131.8, 130.7, 129.21, 129.15, 129.06, 126.4, 32.5; IR (KBr) cm$^{-1}$ 3264, 2914, 1635, 1435; LREIMS C$_{19}$H$_{14}$BrNO$_5$S requires 414.99. Found: 417, 415 ([M$^+$], 5%), 402, 400 ([M-NH$^+$], 100%).

2-[5-(3-Amino-4-iodobenzoyl)-2-phenylthiophene-3-yl]-N-hydroxyacetamide (4)

mp>170° C. (decomp); $^1$H NMR (400 MHz, DMSO-d$_6$) δ 10.69 (s, 1H), 8.87 (s, 1H), 7.71 (d, J=8.2 Hz, 1H), 7.70 (s, 1H), 7.67 (d, J=7.5 Hz, 1H), 7.51 (m, 3H), 7.17 (d, J=2.0 Hz, 1H), 6.75 (dd, J=2.0, 8.0 Hz, 1H), 3.38 (s, 2H); $^{13}$C NMR (100 MHz, DMSO-d$_6$) δ 186.8, 166.3, 149.0, 148.3, 139.9, 138.8, 138.2, 138.1, 132.8, 132.3, 129.1, 129.0, 117.7, 113.5, 88.2, 32.5; IR (KBr) cm$^{-1}$ 3446, 3358, 3218, 2920, 1654, 1608, 1432.

2-[5-(3-Nitro-4-iodobenzoyl)-2-phenylthiophene-3-yl]-N-hydroxyacetamide (5)

mp 147-151° C.; $^1$H NMR (400 MHz, DMSO-d$_6$) δ 10.66 (s, 1H), 8.88 (s, 1H), 8.34 (d, J=7.8 Hz, 1H), 8.30 (s, 1H), 7.79 (m, 2H), 7.68-7.50 (m, 5H), 3.39 (s, 2H); $^{13}$C NMR (100 MHz, DMSO-d$_6$) δ 184.4, 166.2, 153.4, 149.7, 141.8, 139.3, 138.9, 138.0, 133.2, 132.3, 132.1, 129.3, 129.2, 129.0, 124.6, 93.4, 32.4; IR (KBr) cm$^{-1}$ 3245, 2922, 1629, 1533, 1433; LREIMS C$_{19}$H$_{13}$IN$_2$O$_5$S requires 507.96. Found: 508 ([M$^+$], 5%), 493 ([M-NH$^+$], 100%).

[5-(4-Bromobenzoyl)-2-phenylthiophene-3-yl]acetic acid hydrazide (6)

mp 157-161° C.; $^1$H NMR (400 MHz, DMSO-d$_6$) δ 9.23 (s, 1H), 7.80 (d, J=8.4 Hz, 2H), 7.77 (d, J=8.4 Hz, 2H), 7.72 (s, 1H), 7.67 (d, J=7.6 Hz, 2H), 7.49 (m, 3H), 4.25 (brs, 2H), 3.43 (s, 2H); $^{13}$C NMR (100 MHz, CDCl$_3$) δ 186.6, 170.6, 150.3, 140.7, 137.2, 136.3, 132.3, 131.7, 131.6, 130.8, 130.6, 129.1, 129.0, 128.9, 128.8, 127.3, 34.2; IR (KBr) cm$^{-1}$ 3294, 3048, 1635, 1435.

[5-(3-Amino-4-iodobenzoyl)-2-phenylthiophene-3-yl]acetic acid hydrazide (7)

mp 159-165° C.; $^1$H NMR (400 MHz, DMSO-d$_6$) δ 9.13 (s, 1H), 7.62 (d, J=8.0 Hz, 1H), 7.58 (s, 1H), 7.55 (d, J=7.6 Hz, 2H), 7.37 (m, 3H), 7.05 (s, 1H), 6.62 (d, J=7.6 Hz, 1H), 4.12 (brs, 2H), 3.30 (s, 2H); $^{13}$C NMR (100 MHz, DMSO-d$_6$) δ 186.9, 168.8, 148.9, 148.3, 139.8, 138.9, 138.2, 133.1, 132.4, 129.1, 128.9, 117.8, 113.5, 88.2, 33.5; IR (KBr) cm$^{-1}$ 3432, 1628, 1431; LREIMS C$_{19}$H$_{16}$IN$_3$O$_2$S requires 477.00. Found: 477 ([M$^+$], 100%), 446 ([M-N$_2$H$_3^+$], 45%), 246 ([C$_6$H$_3$(NH$_2$)I$^+$], 100%).

[2-Phenyl-5-(2-phenyl-1H-indole-6-carbonyl)thiophene-3-yl]acetic acid methyl ester (23)

To 0.48 g (1.0 mmol) 22 placed in a flask was added 30 mL of Et$_2$NH under stream of N$_2$. The resulting solution was degassed for 20 min with a stream of N$_2$. To this solution was added 164.7 uL (1.5 mmol) of phenylacetylene. The resulting solution was then degassed for 5 min followed by adding 20.9 mg (0.11 mmol) of CuI and 0.12 g (0.1 mmol) of Pd(PPh$_3$)$_4$ at room temperature. The resulting mixture was degassed for 10 min and stirred at room temperature for 4 h. The solvent was evaporated in vacuo, and the residue was purified by flash chromatography (EtOAc/Hex 1:4) to give 0.44 g (98%) of [5-(3-Amino-4-phenylethynylbenzoyl)-2-phenyl-thiophene-3-yl]-acetic acid methyl ester as a yellow solid: mp 146-148° C.; $^1$H NMR (400 MHz, CDCl$_3$) δ 7.66 (s, 1H), 7.55 (m, 2H), 7.47 (m, 5H), 7.37 (m, 4H), 7.23 (m, 2H), 4.48 (s, 2H), 3.71 (s, 3H), 3.68 (s, 2H); $^{13}$C NMR (100 MHz, CDCl$_3$) δ 187.45, 171.3, 149.9, 147.8, 141.2, 138.7, 137.4, 132.8, 132.1, 131.6, 130.4, 129.3, 128.98, 128.94, 128.7, 128.5, 122.8, 118.8, 114.4, 111.8, 97.2, 85.2, 52.3, 34.2.

A solution of 0.81 g (1.79 mmol) of the above compound in 20 mL of dry DMF was degassed with N$_2$ for 15 min followed by adding 0.14 g (0.36 mmol) of PdCl$_2$(PhCN)$_2$. The resulting mixture was degassed for 10 min, heated at 80° C. for 30 min, cooled to room temperature, diluted with 50 mL of H$_2$O, extracted with 3×30 mL of EtOAc, and concentrated in vacuo. The residue was purified by flash chromatography (EtOAc/Hex 1:4) to give 0.49 g (61%) of 23 as a bright yellow solid: mp 183-185° C.; $^1$H NMR (400 MHz, CDCl$_3$) δ 9.50 (s, 1H), 8.19 (s, 1H), 7.79 (d, J=8.3 Hz, 2H), 7.71 (m, 3H), 7.47 (m, 6H), 7.35 (t, J=7.1 Hz, 1H), 6.89 (s, 1H), 3.71 (s, 3H), 3.68 (s, 2H); $^{13}$C NMR (100 MHz, CDCl$_3$) δ 188.2, 171.5, 149.0, 142.1, 141.9, 137.2, 136.4, 132.95, 132.93, 131.7, 131.5, 130.2, 129.3, 129.1, 128.9, 128.8, 128.4, 125.7, 121.9, 120.0, 113.4, 99.9, 52.3, 34.3; IR (KBr) cm$^{-1}$ 3350, 3054, 2947, 1737, 1596, 1436, 1314; LREIMS C$_{28}$H$_{21}$INO$_3$S requires 451.12. Found: 451 ([M$^+$], 100%).

[2-Phenyl-5-(2-phenyl-1H-indole-6-carbonyl)thiophene-3-yl]acetic acid (8)

To a stirred solution of 0.44 g (0.97 mmol) of 23 in 7 mL of MeOH and 7 mL of THF was added 1.5 mL (1.5 mmol) of 1

N NaOH solution. The resulting solution was stirred at room temperature for 4 h. The solvent was removed in vacuo, and the residue was diluted with 10 mL of $H_2O$, acidified to pH~3 with 1N HCl, and extracted with 30 mL of EtOAc. The organic layer was dried over $MgSO_4$, filtered, and concentrated in vacuo. The residue was purified by flash chromatography (EtOAc/Hex 1:1) to afford 0.36 g (87%) of 8: mp 238-240° C.; $^1$H NMR (400 MHz, DMSO-$d_6$) δ 12.5 (brs, 1H), 12.04 (s, 1H), 8.00 (s, 1H), 7.93 (d, J=7.4 Hz, 2H), 7.80 (s, 1H), 7.70 (d, J=8.2 Hz, 1H), 7.59-7.48 (m, 9H), 7.38 (t, J=7.1 Hz, 1H), 7.07 (d, J=1.2 Hz, 1H), 3.69 (s, 2H); $^{13}$C NMR (100 MHz, $CDCl_3$) δ 186.6, 172.0, 147.4, 141.6, 141.0, 136.3, 132.6, 132.2, 131.9, 131.4, 130.4, 129.2, 129.1, 128.8, 128.3, 125.6, 125.4, 120.5, 99.3, 34.1; IR (KBr) cm$^{-1}$ 3417, 3054, 1713, 1596.

N-Hydroxy-2-[2-phenyl-5-(2-phenyl-1H-indole-6-carbonyl)thiophene-3-yl]acetamide (9)

To a stirred solution of 40.1 mg (0.09 mmol) of 8 in 5 mL of dry $CH_2Cl_2$ was added sequentially 140 mg (0.37 mmol) of O-(7-azabenzotriazole-1-yl)-N,N,N',N'-tetramethyluronium hexafluorophosphate (HATU), 49.5 mg (0.37 mmol) of HOBt, and 91 uL (0.55 mmol) of DIEA. The resulting solution was stirred at room temperature for 10 min followed by adding 50.5 mg (0.18 mmol) of O-tritylhydroxylamine. After stirring at the same temperature for 30 min, the solvent was removed in vacuo and the residue was purified by flash chromatography (EtOAc/Hex 1:4) to give O-trityl hydroxyamic acid of 8 in a quantitative yield. The resulting oily product was treated with 5 mL of 1:2 mixture of AcOH/2,2,2-trifluoroethanol at room temperature for 24 h. After evaporation of the solvent in vacuo, the residue was dissolved in $CH_2Cl_2$ and washed with 10 mL of a saturated $NaHCO_3$ solution. The organic layer was dried over $MgSO_4$, filtered, and concentrated in vacuo. The residue was purified by flash chromatography (MeOH/EtOAc 1:9) to give 12.7 mg (54% over two steps) of 9 as a bright yellow powder: mp~150° C. (decomp); $^1$H NMR (400 MHz, DMSO-$d_6$) δ 12.1 (s, 1H), 11.68 (brs, 1H), 8.95 (brs, 1H), 7.99 (s, 1H), 7.93 (d, J=7.8 Hz, 2H), 7.81 (s, 1H), 7.70 (m, 3H), 7.66-7.48 (m, 6H), 7.38 (t, J=7.0 Hz, 1H), 7.08 (s, 1H), 3.41 (s, 2H); $^{13}$C NMR (100 MHz, $CDCl_3$) δ 187.4, 167.1, 147.9, 142.3, 141.6, 138.1, 136.9, 133.3, 133.2, 132.8, 132.1, 131.4, 131.0, 129.8, 129.7, 129.0, 127.7, 126.2, 121.1, 120.7, 113.9, 99.9, 33.2; IR (KBr) cm$^{-1}$ 3422-3241, 2902, 1596, 1433, 1322.

{5-[1-(4-Aminobutyl)-2-phenyl-1H-indole-6-carbonyl]-2-phenylthiophene-3-yl}acetic acid hydroiodide (10)

To a stirred solution of 0.20 g (0.45 mmol) of 23 in 10 mL of anhydrous $CH_3CN$ was added 1.36 g of CsF-Celite under $N_2$ followed by adding 0.11 g (0.45 mmol) of N-Boc-1-bromo-4-butylamine. The resulting mixture was refluxed under $N_2$ for 48 h. The solvent was evaporated under reduced pressure, and the residue was purified by flash chromatography (EtOAc/Hex 1:4) to give 0.07 g (33% based on the recovered starting material) of {5-[1-(4-N-Boc-aminobutyl)-2-phenyl-1H-indole-6-carbonyl]-2-phenylthiophene-3-yl}acetic acid methyl ester as a yellow foam: $^1$H NMR (400 MHz, $CDCl_3$) δ 8.04 (s, 1H), 7.73 (m, 3H), 7.50 (m, 8H), 6.60 (s, 1H), 4.51 (br s, 1H), 4.28 (t, J=6.7 Hz, 2H), 3.72 (s, 3H), 3.70 (s, 2H), 2.97 (m, 2H), 1.73 (q, J=7.5 Hz, 2H), 1.38 (s, 9H), 1.31 (q, J=6.3 Hz, 2H); $^{13}$C NMR (100 MHz, $CDCl_3$) δ 188.1, 171.5, 155.8, 148.8, 144.9, 142.2, 136.9, 136.6, 132.9, 132.4, 131.7, 131.1, 130.1, 129.3, 128.9, 128.8, 128.7, 128.6, 121.4, 120.2, 112.3, 102.7, 79.1, 52.3, 43.7, 39.9, 34.3, 28.3, 27.4, 27.2; IR (KBr) cm$^{-1}$ 3410-3380, 2930, 1738, 1709, 1625, 1600, 1437.

To a stirred solution of 56.9 mg (9.1×10$^{-5}$ mol) of the above ester in 2 mL MeOH was added 91.4 uL of 1N NaOH. The resulting mixture was refluxed for 2.5 h. The solvent was removed in vacuo. The residue was diluted with 2.5 mL of $H_2O$, neutralized with 91.4 uL of 1N HCl, and extracted with 20 mL of EtOAc. The organic layer was dried over $MgSO_4$, filtered, and concentrated in vacuo to give 41.3 mg (75%) of {5-[1-(4-tert-butoxycarbonylamino-butyl)-2-phenyl-1H-indole-6-carbonyl]-2-phenylthiophene-3-yl}acetic acid as a yellow solid: mp 167-169° C.; $^1$H NMR (400 MHz, $CDCl_1$) δ 8.00 (s, 1H), 7.73 (m, 2H), 7.49 (m, 11H), 6.60 (s, 1H), 4.14 (t, J=7.0 Hz, 2H), 3.68 (s, 2H), 3.14 (m, 2H), 1.96 (m, 2H), 1.45 (s+m, 9+2H); IR (KBr) cm$^{-1}$ 3433, 3303, 2977, 1714, 1601.

To a stirred solution of 30.0 mg of the above acid (4.93×10$^{-5}$ mol) in 1.0 mL of $CHCl_3$ was added 14 uL (9.86×10$^{-5}$ mol) of TMSI at room temperature. After stirring at room temperature for 6 h, precipitates were collected by filtration, washed with $CHCl_3$, and dried under high vacuum to give 14.9 mg (47%) of 10 in its HI salt form as a brown powder: mp>150° C. (decomp); $^1$H NMR (400 MHz, DMSO-$d_4$) δ 12.9 (brs, 1H), 8.12 (s, 1H), 7.81 (s, 1H), 7.75 (d, J=8.2 Hz, 1H), 7.62-7.49 (m, 11H), 6.71 (s, 1H), 4.36 (t, J=7.0 Hz, 2H), 3.70 (s, 2H), 3.44 (brs, 3H), 2.62 (h, J=5.1 Hz, 2H), 1.65 (m, 2H), 1.29 (m 2H); $^{13}$C NMR (100 MHz, DMSO-$d_6$) δ 186.9, 172.1, 147.5, 144.5, 140.9, 138.5, 136.2, 132.5, 132.1, 131.8, 131.1, 130.5, 129.2, 129.16, 129.06, 128.9, 128.8, 120.6, 120.2, 112.5, 102.6, 43.1, 38.4, 34.1, 26.7, 24.3; IR (KBr) cm$^{-1}$ 3438, 3057, 1718, 1590; LREIMS $C_{31}H_{28}N_2O_3S$ (neutral form) requires 508.18. Found: 490 ([M$^+$-$H_2O$], 60%).

{5-[1-(4-Aminobutyl)-2-phenyl-1H-indole-6-carbonyl]-2-phenylthiophene-3-yl}acetic acid hydrazide hydrochloride (11)

To a stirred solution of 53.2 mg (8.54×10$^{-5}$ mol) of {5-[1-(4-N-Boc-aminobutyl)-2-phenyl-1H-indole-6-carbonyl]-2-phenylthiophene-3-yl}acetic acid methyl ester in 1.5 mL of MeOH and 1.5 mL of THF was added 415 uL of hydrazine hydrate at room temperature. After stirring at room temperature for 4.5 h, the solvent was removed in vacuo. The residue was purified by flash chromatography (EtOAc) to afford 49.7 mg (93%) of acid hydrazide as a yellow foam. To a solution of 60.0 mg of the acid hydrazide (9.6×10$^{-5}$ mol) in 1 mL of MeOH was added 16 uL (19.3×10$^{-5}$ mol) of 12N HCl at room temperature. After stirring at room temperature for 17 h, the solvent was removed in vacuo. The deep red residue was dissolved in 10 mL of EtOAc followed by extraction with 5 mL of $H_2O$. The aqueous layer was filtered through a Celite pad. The filtrate was freeze-dried to afford 11.5 mg (20%) of 11 as a dark red-brown powder (dihydrochloride): $^1$H NMR (400 MHz, DMSO-4) δ 11.35 (s, 1H), 10.3 (brs, 3H), 8.13 (s, 1H), 7.89-7.49 (m, 14H), 6.70 (s, 1H), 4.36 (t, J=7.4 Hz, 2H), 3.74 (s, 2H), 2.62 (m, 2H), 1.68 (m, 2H), 1.35 (m, 2H); $^{13}$C NMR (100 MHz, DMSO-$d_6$) δ 186.9, 168.9, 147.9, 144.6, 141.1, 137.9, 136.2, 132.3, 131.8, 131.3, 131.1, 130.4, 129.2, 129.18, 129.0, 128.9, 128.8, 120.6, 120.3, 112.6, 102.5, 43.2, 38.3, 32.9, 26.8, 24.3; IR (KBr) cm$^{-1}$ 3421, 2936, 1700, 1594, 1446.

2-{5-[1-(4-Aminobutyl)-2-phenyl-1H-indole-6-carbonyl]-2-phenylthiophene-3-yl}-N-hydroxyacetamide hydrochloride (12)

To a stirred solution of 43.0 mg (7.1×10$^{-5}$ mol) of {5-[1-(4-tert-butoxycarbonylamino-butyl)-2-phenyl-1H-indole-6- carbonyl]-2-phenylthiophene-3-yl}acetic acid (N-Boc-protected 10) in 5 mL of dry $CH_2Cl_2$ was added sequentially 107.4 mg ($2.83 \times 10^{-4}$ mol) of HATU, 38.2 mg ($2.83 \times 10^{-4}$ mol) of HOBt, and 70 uL ($4.24 \times 10^{-4}$ mol) of DIEA at room temperature. The resulting mixture was stirred at room temperature for 10 min followed by adding 38.9 mg ($1.41 \times 10^{-4}$ mol) of O-tritylhydroxylamine. After stirring at room temperature for 30 min, the solvent was removed in vacuo, and the residue was purified by flash chromatography (EtOAc/Hex 1:4) to give 32.0 mg (57%) of O-tritylhydroxamate as a yellow foam. The resulting material was treated with 1.5 mL of a mixture of AcOH/TFE (1:2) at room temperature for 48 h. The resulting mixture was concentrated under reduced pressure, and the residue was purified by flash chromatography (MeOH/AcOEt 1:9) to afford 23.2 mg (92%) of the hydroxamate: mp~95° C. (decomp); $^1$H NMR (400 MHz, DMSO-$d_6$) δ 10.72 (s, 3H), 8.90 (s, 1H), 8.11 (s, 1H), 7.82 (s, 1H), 7.45-7.48 (m, 12H), 6.68 (s, 1H), 1.67 (s, 1H), 4.31 (t, J=7.0 Hz, 2H), 3.42 (s, 2H), 2.74 (q, J=6.2 Hz, 2H), 1.58 (p, J=7.4 Hz, 2H), 1.29 (s, 9H), 1.16 (m, 2H); $^{13}$C NMR (100 MHz, DMSO-$d_6$) δ 186.9, 166.4, 155.5, 147.4, 144.6, 140.9, 137.9, 136.2, 132.6, 132.5, 131.9, 130.9, 130.5, 129.1, 129.06, 128.9, 128.8, 128.6, 120.5, 120.2, 112.5, 102.4, 77.4, 43.3, 32.6, 28.2, 27.1, 26.7; IR (KBr) $cm^{-1}$ 3370-3260, 2929, 1677, 1448.

To a stirred solution of 75 mg (0.12 mmol) of 2-{5-[1-(4-N-Boc-Aminobutyl)-2-phenyl-1H-indole-6-carbonyl]-2-phenylthiophene-3-yl}-N-hydroxyacetamide in ethyl acetate (3 ml) was added 100 µL (1.2 mmol) of 12 N HCl. The reaction mixture was stirred at room temperature for 30 min. The solvent was removed in vacuo and the residue was then dissolved in water. Some insolubles were observed and were removed by filtration through a pad of Celite. The filtrate was freeze-dried under high vacuum to give 61 mg (91% yield) of the desired product as a fine brown powder; mp>155° C. (decomp); $^1$H NMR (400 MHz, DMSO-$d_6$) δ 10.89 (s, 1H), 9.02 (s, 1H), 8.12 (s, 1H), 7.84 (s, 1H), 7.76-7.49 (m, 12H), 6.70 (s, 1H), 4.34 (t, J=6.9 Hz, 2H), 3.45 (s, 2H), 2.64 (h, J=6.4 Hz, 2H), 1.69 (m 2H), 1.36 (m, 2H); $^{13}$C NMR (100 MHz, DMSO-$d_6$) δ 187.7, 167.4, 148.0, 145.2, 141.8, 138.4, 136.8, 133.3, 133.2, 132.5, 131.7, 131.1, 120.8, 129.7, 129.6, 129.4, 121.2, 121.1, 113.3, 103.3, 43.9, 39.1, 33.2, 27.5, 25.0; IR (KBr) $cm^{-1}$ 3404, 3252, 3053, 2925, 1617, 1586, 1448.

2-{5-[1-(5-aminopentyl)-2-phenyl-1H-indole-6-carbonyl]-2-phenylthiophene-3-yl}-N-hydroxy-acetamide hydrochloride (13)

A suspension of 0.37 g (0.81 mmol) of 23, 0.23 g (0.88 mmol, 1.1 eq.) of N-Boc-1-bromo-5-pentylamine and 2.00 g (8.0 mmol, 10 eq.) of CsF-Celite in acetonitrile (15 mL) was refluxed under $N_2$ for 24 h. The suspension was then allowed to cool to room temperature and filtered through a pad of Celite. The filtrate was concentrated in vacuo and the residue was purified by flash column chromatography ($SiO_2$, 4:1 Hex/EtOAc) to give 0.40 g (77% yield) of 2-{5-[1-(5-N-Boc-aminopentyl)-2-phenyl-1H-indole-6-carbonyl]-2-phenylthiophene-3-yl}acetic acid methyl ester as a yellow foam. $R_f$=0.10 (4:1 Hex/EtOAc); $^1$H NMR (400 MHz, CDCl$_3$) δ 7.96 (s, 1H), 7.70-7.62 (m, 3H), 7.47-7.34 (m, 10H), 6.52 (s, 1H), 4.37 (brs, 1H), 4.17 (t, J=7.0 Hz, 2H), 3.64 (s, 3H), 3.62 (s, 2H), 2.90 (dt, J=4.7, 5.6, 2H), 1.69-1.62 (m, 2H), 1.34 (s, 9H), 1.28-1.21 (m, 2H), 1.12-1.04 (m, 2H); $^{13}$C NMR (100 MHz, CDCl$_3$) δ 188.2, 171.7, 156.2, 149.0, 145.1, 142.2, 137.2, 137.0, 133.2, 133.0, 132.4, 131.9, 131.3, 130.4, 129.6, 129.5, 129.2, 129.1, 129.0, 128.8, 121.7, 120.3, 112.5, 102.8, 52.5, 44.1, 34.5, 30.0, 29.7, 28.6, 24.1; IR (KBr) $cm^{-1}$ 3376, 2929, 2858, 1739, 1708, 1624, 1561, 1513.

To a stirred solution of 0.26 g (0.40 mmol) of the above methyl ester in methanol (20 mL) was added 1.5 mL (1.5 mmol, 3.7 eq.) of 1.0 N NaOH. The resulting solution was stirred under reflux for 4 h then allowed to cool to room temperature. The solvent was removed in vacuo and the residue dissolved in 40 mL of EtOAc plus 30 ml of water. To this biphasic mixture, 1.5 mL (1.5 mmol) of 1.0 N HCl was added. The phases were separated and the aqueous phase was washed with 40 mL of EtOAc. The organic phases were combined and concentrated in vacuo. The residue was purified by flash column chromatography ($SiO_2$, 1:1 Hex/EtOAc) to give 0.25 g (quantitative yield) of 2-{5-[1-(5-N-Boc-aminopentyl)-2-phenyl-1H-indole-6-carbonyl]-2-phenylthiophene-3-yl}acetic acid as a yellow foam. $R_f$=0.29 (1:1 Hex/EtOAc); $^1$H NMR (400 MHz, CDCl$_3$) δ 12.58 (brs, 1H) 8.03 (s, 1H), 7.78-7.31 (m, 13H), 6.53 (s, 1H), 4.78 (brs, 1H), 4.11 (t, J=8.0 Hz, 2H), 3.58 (s, 2H), 3.02 (m, 2H), 1.81-1.71 (m, 2H), 1.42 (s, 9H), 1.40-1.34 (m, 2H), 1.18-1.09 (m, 2H); $^{13}$C NMR (100 MHz, CDCl$_3$) δ 188.2, 175.5, 159.2, 148.8, 144.8, 143.1, 136.8, 136.4, 133.3, 132.8, 131.8, 130.9, 130.7, 129.7, 129.4, 129.2, 129.0, 128.9, 121.3, 120.3, 113.4, 103.0, 81.4, 64.6, 45.1, 41.3, 34.5, 30.5, 29.9, 28.6, 24.5; IR (KBr) $cm^{-1}$ 3371, 2928, 2856, 1711, 1624, 1533, 1479.

To a stirred solution of 0.22 g (0.35 mmol) of the above acid in DCM (20 mL) were added sequentially 0.15 g (0.39 mmol, 1.1 eq.) of HBTU, 0.11 g (0.39 mmol, 1.1 eq) of O-tritylhydroxylamine and 0.12 mL (0.68 mmol, 1.9 eq) of diisopropylethylamine (DIEA). The reaction mixture was stirred at room temperature for 1.5 h and then water (15 mL) and brine (5 mL) were added. The phases were separated and the aqueous phase washed with DCM (20 mL). The organic phases were combined and concentrated in vacuo. The residue was purified by flash column chromatography ($SiO_2$, 2:1 Hex/EtOAc) to give 0.21 g (69% yield) of 2-{5-[1-(5-N-Boc-aminopentyl)-2-phenyl-1H-indole-6-carbonyl]-2-phenylthiophene-3-yl}-O-tritylhydroxy-acetamide as a yellow solid. $R_f$=0.39 (2:1 Hex/EtOAc); mp~110° C.; $^1$H NMR (400 MHz, CDCl$_3$) δ 7.97 (s, 1H), 7.68-7.18 (m, 23H), 6.56 (s, 1H), 4.37 (brs, 1H), 4.16 (t, J=7.0 Hz, 2H), 3.60 (s, 2H), 2.90 (dt, J=4.7, 5.6, 2H), 1.68-1.59 (m, 2H), 1.33 (s, 9H), 1.29-1.19 (m, 2H), 1.12-1.02 (m, 2H); $^{13}$C NMR (100 MHz, CDCl$_3$) δ 188.4, 169.7, 156.2, 147.1, 145.1, 142.2, 137.1, 136.9, 136.8, 136.5, 133.5, 133.2, 132.7, 131.9, 131.3, 130.4, 129.6, 129.4, 129.2, 129.1, 129.0, 128.9, 128.7, 128.4, 128.3, 128.2, 128.1, 127.8, 127.7, 127.4, 121.7, 120.3, 112.6, 103.0, 102.9, 64.2, 49.1, 48.9, 46.1, 44.1, 40.5, 36.5; IR (KBr) $cm^{-1}$ 3349, 2972, 2931, 2863, 1708, 1624, 1479, 1390.

A solution of 0.20 g (0.22 mmol) of the above product in 2:1 mixture of 2,2,2-trifluoroethanol/acetic acetic (40 mL) was stirred at room temperature overnight. The solvent was removed in vacuo and the residue was dried under high vacuum for 1.5 h to get rid of most of the acetic acid. The crude dry residue was then purified by flash column chromatography ($SiO_2$, 1:1 Hex/EtOAc) to give 87 mg (61% yield) of 2-{5-[1-(5-N-Boc-aminopentyl)-2-phenyl-1H-indole-6-carbonyl]-2-phenylthiophene-3-yl}-N-hydroxy-acetamide as a yellow solid. $R_f$=0.15 (1:1 Hex/EtOAc); mp 223° C.; $^1$H NMR (400 MHz, CDCl$_3$) δ 9.62 (br s, 1H), 8.51 (br, s, 1H), 7.99 (s, 1H), 7.78-7.36 (m, 13H), 6.57 (s, 1H), 4.58 (br, s, 1H), 4.21 (t, J=7.0 Hz, 2H), 3.52 (s, 2H), 2.96 (t, J=5.7, 2H), 1.79-1.64 (m, 2H), 1.36 (s, 9H), 1.31-1.23 (m, 2H), 1.14-1.08 (m, 2H); $^{13}$C NMR (100 MHz, CDCl$_3$) δ 188.0, 168.2, 156.4, 149.1, 145.0, 143.1, 136.5, 133.0, 132.7, 132.0, 131.1, 130.2, 129.6, 129.2, 129.0, 128.7, 121.4, 120.3, 113.1, 103.0, 79.6, 64.2, 60.8, 44.2, 40.5, 29.9, 28.6, 24.0; IR (KBr) cm$^{-1}$ 3245, 2927, 2856, 1674, 1623, 1533, 1478, 1390.

To a stirred solution of 69 mg (0.11 mmol) of the above product in EtOAc (3 mL) was added 90 µL (1.1 mmol, 10 eq.) of 12 N HCl. The reaction mixture was stirred at room temperature for 30 min. The solvent was removed in vacuo and the residue was then dissolved in water. Some insolubles were observed and were removed by filtration through a pad of Celite. The filtrate was freeze-dried under high vacuum to give 54 mg (87% yield) of the desired final product 13 as a fine brown powder; mp~139 (decomp); $^1$H NMR (400 MHz, DMSO-d$_6$) δ 10.87 (s, 1H), 8.97 (br s, 1H), 8.08 (s, 1H), 7.82-7.47 (m, 13H), 6.68 (s, 1H), 4.29 (t, J=7.0 Hz, 2H), 3.44 (s, 2H), 3.35 (s, 2H), 2.62 (h, J=6.0, 2H), 1.64-1.58 (m, 2H), 1.45-1.36 (m, 2H), 1.21-1.09 (m, 2H); $^{13}$C NMR (100 MHz, DMSO-d$_6$) δ 187.6, 167.3, 148.1, 145.2, 141.6, 138.6, 136.8, 133.4, 133.2, 132.6, 131.6, 131.0, 129.8, 129.7, 129.6, 129.5, 129.4, 121.2, 121.0, 113.1, 103.1, 39.6, 39.1, 33.2, 29.8, 27.1, 23.7; IR (KBr) cm$^{-1}$ 3395, 2936, 1662, 1616, 1596, 1477, 1380.

2-{5-[1-(6-Aminohexyl)-2-phenyl-1H-indole-6-carbonyl]-2-phenylthiophene-3-yl}-N-hydroxyacetamide hydrochloride (14)

The titled compound obtained as a fine brown powder was synthesized according to the procedure for 13 in 78% yield from the Boc-protected precursor; mp>137 (decomp); $^1$H NMR (400 MHz, DMSO-d$_6$) δ 10.79 (s, 1H), 8.92 (br s, 1H), 8.09 (s, 1H), 7.81-7.48 (m, 13H), 6.68 (s, 1H), 4.32 (t, J=7.0 Hz, 2H), 3.42 (s, 2H), 3.34 (s, 2H), 2.59 (h, J=6.0, 2H), 1.61-1.57 (m, 2H), 1.37-1.31 (m, 2H), 1.11-1.07 (m, 4H); $^{13}$C NMR (100 MHz, DMSO-d$_6$) δ 187.6, 167.2, 148.1, 145.3, 141.5, 138.6, 136.9, 133.4, 133.2, 132.7, 131.7, 131.1, 129.83, 129.79, 129.74, 129.6, 129.4, 121.2, 121.0, 113.1, 103.1, 44.0, 39.2, 33.3, 30.1, 27.4, 26.2, 25.9; IR (KBr) cm$^{-1}$ 3423, 2933, 1655, 1648, 1597, 1560, 1477.

Referring to FIG. 8, wherein R corresponds to the moieties listed as "a-m" at the bottom of FIG. 8:

Methyl 2-(2-bromo-5-(4-iodo-3-nitrobenzoyl)thiophen-3-yl)acetate (25)

To a stirred solution of 230 mg (1 mmol) methyl (2-bromothiophene-3-yl)acetate and 310 mg (1 mmol) 4-iodo-3-nitrobenzoyl chloride in 15 mL of dry CH$_2$Cl$_2$ was added 432 mg of AlCl$_3$ (4 mmol) in four portions at room temperature. The resulting mixture was stirred overnight. The reaction mixture was slowly poured onto 5 g of ice and allowed to warm to room temperature. The organic layer was dried over MgSO$_4$, filtered, and then concentrated in vacuo. The residue was purified by flash chromatography. (Hex/EtOAc=1:5) to give 310 mg of product as a light yellow solid (yield 60%).

$^1$H NMR (400 MHz, CDCl$_3$) δ 3.68 (s, 2H), 3.74 (s, 3H), 7.48 (s, 1H), 7.69 (dd, 1H, J=2.0, 8.2 Hz), 8.21 (d, 1H, J=8.0 Hz), 8.27 (d, J=2.0 Hz, 1H).

Methyl 2-(2-bromo-5-(3-nitro-4-(phenylethynyl)benzoyl)thiophen-3-yl)acetate (26)

A solution of methyl 2-(2-bromo-5-(4-iodo-3-nitrobenzoyl)thiophen-3-yl)acetate 508 mg (1 mmol), phenylacetylene (95 mg, 0.95 mmol), Pd(PPh$_3$)$_2$Cl$_2$ (70 mg, 0.1 mmol, 10% equive), K$_2$CO$_3$ (138 mg, 1 mmol), and Et$_3$N (101 mg, 1 mmol) in DMF (5 mL) was stirred for 24 h at room temperature. H$_2$O (5 mL) was added to the mixture and then extracted with AcOEt (3×10 mL). The combined organic layers were washed with saturated aqueous NaCl solution, dried over anhydrous MgSO$_4$, and concentrated. The residue was purified by flash chromatography (Hex/AcOEt=1:5) to form 340 mg of the product as solid foam (yield 70.6%).

$^1$H NMR (400 MHz, CDCl$_3$) δ 3.69 (s, 2H), 3.75 (s, 3H), 7.41-7.4 (m, 3H), 7.51 (s, 1H), 7.62-7.64 (m, 2H), 7.85 (d, 1H, J=8.4 Hz), 8.04 (dd, 1H, J=8.0, 1.6 Hz), 8.54 (d, 1H, J=1.6 Hz)

Methyl-(2-bromo-5-(2-phenyl-1H-indole-6-carbonyl)thiophene-3-yl)acetate (27)

To a solution of methyl 2-(2-bromo-5-(3-nitro-4(phenylethyl)benzoyl)thiophen-3-yl)acetate (482 mg, 1 mmol) in 100 mL EtOAc was added 945 mg (5 mmol, 5.0 equiv) of stannous chloride dihydrate. The resulting mixture was refluxed for 1 h under N$_2$. The reaction mixture was poured onto 20 g ice, and basified with saturated NaHCO$_3$ solution to pH 8. The white milky mixture was filtered through a Celite pad to remove the tin oxides. The organic layer was dried over MgSO$_4$, filtered and then concentrated to form 434 mg of methyl (2-bromo-5-(3-amino-4(phenylethynl)benzoyl)thiophen-3-yl)acetate as the yellow foam (yield 96%).

$^1$H NMR (400 MHz, CDCl$_3$) δ 3.66 (s, 2H), 3.72 (s, 3H), 4.88 (br, 2H), 7.24 (m, 1H), 7.39-7.36 (m, 4H), 7.49-7.47 (m, 2H), 7.56-7.54 (m, 2H).

To a 25 mL flask under N$_2$ containing freshly distilled toluene (10 mL) were added methyl (2-bromo-5-(3-amino-4-(phenylethynyl)benzoyl)thiophen-3-yl)acetate 227 mg (0.5 mmol) and indium tribromide (18 mg, 0.05 mmol, 10% equiv). The resulting mixture was refluxed for 1 h. After removing the solvent, the crude product was purified by MPLC (Hex/AcOEt=1:4) to afford 192 mg of product as a yellow solid (yield 85%).

$^1$H NMR (400 MHz, CDCl$_3$) δ 3.68 (s, 2H), 3.74 (s, 3H), 6.90 (d, 1H, J=1.2 Hz), 7.41 (t, 1H, J=7.2 Hz), 7.51 (t, 2H, J=7.2 Hz), 7.55 (s, 1H), 7.68 (m, 2H), 7.77 (m, 2H), 8.02 (s, 1H), 8.91 (br, 1H).

Methyl 2-(2-bromo-5-(1-(4-(1,3-dioxo-2,3-dihydro-1H-inden-2-ylamino)butyl)-2-phenyl-1H-indole-6-carbonyl)thiophene-3-yl)acetate (28)

To a stirred solution of 453 mg (1 mmol) of methyl-(2-bromo-5-(2-phenyl-1H-indole-6-carbonyl)thiophene-3-yl)acetate in 10 mL of anhydrous CH$_3$CN was added 1.25 g of CsF-Celite under N$_2$, and then followed by 295 mg (1 mmol) 2-(4-bromobutylamino)-1H-indene-1,3(2H)-dione. The resulting mixture was refluxed for 5 h. The mixture was filtered and washed with CH$_3$CN (5 mL×3), the filtrate was evaporated under reduced pressure, and the residue was purified by MPLC (EtOAc/Hex 1:4) to give 280 mg product as a yellow solid (yield 42%).

$^1$H NMR (400 MHz, CDCl$_3$) δ 1.50 (m, 2H), 1.72 (m, 2H), 3.51 (t, 2H, J=6.8 Hz), 3.71 (s, 2H), 3.79 (s, 3H), 4.32 (t, 2H, J=6.8 Hz), 6.59 (s, 1H), 7.43 (m, 2H), 7.50 (m, 3H), 7.59 (s, 1H), 7.72 (m, 4H), 7.80 (m, 2H), 7.97 (s, 1H).

Methyl 2-(5-(4-(1,3-dioxo-2,3-dihydro-1H-inden-2-ylamino)butyl)-2-pheny-1H-indole-6-carbonyl-2-(3-hydroxyphenyl)thiophen-3-yl)acetate (29m)

To the solution of 3-hydroxyphenylboronic acid (28 mg, 0.2 mmol) in 1 mL EtOH (degassed with N$_2$), was added a solution of methyl 2-(2-bromo-5-(1-(4-(1,3-dioxo-2,3-dihydro-1H-inden-2-ylamino)butyl)-2-phenyl-1H-indole-6-carbonyl)thiophene-3-yl)acetate (111 mg, 0.17 mmol) in 5 mL toluene, and then followed by Pd(PPh$_3$)$_2$Cl$_2$ (11.6 mg, 0.017 mmol, 10% equive) and Na$_2$CO$_3$ (35 mg, 0.33 mmol). The reaction mixture was refluxed for 3 h and then the solvent was removed under reduced pressure. The residue was purified by MPLC (EtOAc/Hex 1:2) to afford 98 mg of the product as a yellow solid (yield 89%). $^1$H NMR (400 MHz, CDCl$_3$) δ 1.49 (m, 2H), 1.68 (m, 2H), 3.43 (t, 2H, J=7.2 Hz), 3.62 (s, 2H), 3.69 (s, 3H), 4.23 (t, 2H, J=7.2 Hz), 6.51 (s, 1H), 6.84 (m, 1H), 6.98 (m, 1H), 7.07 (m, 1H), 7.24 (t, 1H, J=7.6 Hz), 7.42-7.35 (m, 5H), 7.64-7.59 (m, 4H), 7.71-7.70 (m, 3H), 7.97 (s, 1H), 9.40 (s, 1H).

2-(5-1-(4-Aminobutyl)-2-phenyl-1H-indole-6-carbonyl)-2-(3-hydroxyphenyl)-thiophen-3-yl)-N-hydroxyacetamide TFA salt (30m)

To a stirred solution of methyl 2-(5-(4-(1,3-dioxo-2,3-dihydro-1H-inden-2-ylamino)butyl)-2-pheny-1H-indole-6-carbonyl-2-(3-hydroxyphenyl)thiophen-3-yl)acetate (34 mg, 0.05 mmol) in THF/MeOH (1 mL each), 0.5 mL 50% aqueous solution of NH$_2$OH was added, followed by a catalytic amount of KCN and then the resulting mixture was stirred at ambient temperature overnight. The solvent was removed in vacuo, the residue washed with water (3×5 mL), the residue was purified by HPLC (Phneomenex Gemini 5 μm C18 21×250 mm) by eluting with gradient of acetonitrile, water (0.0045% TFA). The product was obtained as a yellow powder (25 mg, 81% yield).

$^1$H NMR (400 MHz, CD$_3$OD) δ 1.48 (m, 2H), 1.79 (m, 2H), 2.8 (t, 2H, J=7.6 Hz), 3.54 (s, 2H), 4.42 (t, 2H, J=7.6 Hz), 6.65 (s, 1H), 6.88 (dd, 1H, J=1.6, 8.0 Hz), 6.96 (m, 1H), 7.01 (d, 1H, J=7.2 Hz), 7.32 (t, 1H, J=8.0 Hz), 7.49-7.60 (m, 5H), 7.66 (dd, J=1.0, 8.2 Hz), 7.74 (d, 1H, J=8.2 Hz), 7.81 (s, 1H), 8.10 (s, 1H).

2-(5-1-(4-Aminobutyl)-2-phenyl-1H-indole-6-carbonyl)-2-aminopyridin-4-yl)thiophen-3-yl)-N-hydroxyacetamide TFA salt (30a)

$^1$H NMR (400 MHz, CD$_3$OD) δ 1.45 (m, 2H), 1.77 (m, 2H), 2.77 (t, 2H, J=7.2 Hz), 3.63 (s, 2H), 4.43 (t, 2H, J=7.2 Hz), 6.66 (s, 1H), 7.14 (d, 1H, J=6.8 Hz), 7.27 (s, 1H), 7.59-7.49 (m, 5H), 7.70 (d, 1H, J=8.0 Hz), 7.75 (d, 1H, J=8.0 Hz), 7.84 (s, 1H), 7.95 (d, 1H, J=6.4 Hz), 8.10 (s, 1H).

2-(5-1-(4-Aminobutyl)-2-phenyl-1H-indole-6-carbonyl)-2-(pyrimidin-5-yl)thiophen-3-yl)-N-hydroxyacetamide TFA salt (30b)

$^1$H NMR (400 MHz, DMSO-d$_6$) δ 1.30 (m, 2H), 1.64 (m, 2H), 2.63 (t, 2H, J=7.6 Hz), 3.42 (s, 2H), 4.36 (t, 2H, J=6.8 Hz), 6.71 (s, 1H), 7.60-7.50 (m, 6H), 7.77 (d, 1H, J=8.0 Hz), 7.90 (s, 1H), 8.12 (s, 1H), 9.14 (s, 2H), 9.30 (s, 1H), 10.21 (s, 1H), 10.83 (s, 1H).

2-(5-1-(4-Aminobutyl)-2-phenyl-1H-indole-6-carbonyl)-2-(2-aminopyrimidin-5-yl)thiophen-3-yl)-N-hydroxyacetamide TFA salt (30c)

$^1$H NMR (400 MHz, DMSO-d$_6$) δ 1.30 (m, 2H), 1.64 (m 2H), 2.64 (t, 2H, J=7.6 Hz), 3.46 (s, 2H), 4.34 (t, 2H, J=7.6 Hz), 6.70 (s, 1H), 7.13 (br, 2H), 7.60-7.50 (m, 6H), 7.75 (d, 1H, J=8.2 Hz), 7.82 (s, 1H), 8.09 (s, 1H), 8.52 (s, 2H), 10.11 (s, 1H), 10.83 (s, 1H).

2-(5-1-(4-Aminobutyl)-2-phenyl-1H-indole-6-carbonyl)-2-(2-(methylthio)pyrimidin-5-yl)thiophen-3-yl)-N-hydroxyacetamide TFA salt (30d)

$^1$H NMR (400 MHz, CD$_3$OD) δ 1.46 (m, 2H), 1.81 (m, 2H), 2.62 (s, 3H), 2.81 (t, 2H, J=7.6 Hz), 3.51 (s, 2H), 4.42 (t, 2H, J=7.6 Hz), 6.66 (s, 1H), 7.59-7.51 (m, 5H), 7.66 (d, 1H, J=8.2 Hz), 7.75 (d, 1H, J=8.2 Hz), 7.87 (s, 1H), 8.09 (s, 1H), 8.81 (s, 2H).

2-(5-1-(4-Aminobutyl)-2-phenyl-1H-indole-6-carbonyl)-2-(2-methoxypyrimidin-5-yl)thiophen-3-yl)-N-hydroxyacetamide TFA salt (30e)

$^1$H NMR (400 MHz, CD$_3$OD) δ 1.43 (m, 2H), 1.80 (m, 2H), 2.79 (t, 2H, J=7.2 Hz), 3.49 (s, 2H), 4.09 (s, 3H), 4.40 (t, 2H, J=7.2 Hz), 6.66 (s, 1H), 7.59-7.52 (m, 5H), 7.66 (d, 1H, J=8.2 Hz), 7.76 (d, 1H, J=8.2 Hz), 7.86 (s, 1H), 8.09 (s, 1H), 8.80 (s, 2H).

2-(5-1-(4-Aminobutyl)-2-phenyl-1H-indole-6-carbonyl)-2-(pyridin-4-yl)thiophen-3-yl)-N-hydroxyacetamide TFA salt (30f)

$^1$H NMR (400 MHz, CD$_3$OD) δ 1.48 (m, 2H), 1.79 (m, 2H), 2.81 (t, 2H, J=7.6 Hz), 3.63 (s, 2H), 4.40 (t, 2H, J=7.2 Hz), 6.67 (s, 1H), 7.60-7.50 (m, 5H), 7.72 (dd, 1H, J=1.0, 8.2 Hz), 7.76 (d, 1H, J=8.2 Hz), 7.80 (m, 1H), 7.88 (s, 1H), 7.95 (d, 1H, J=6.4 Hz), 8.12 (s, 1H), 8.79 (m, 2H).

2-(5-1-(4-Aminobutyl)-2-phenyl-1H-indole-6-carbonyl)-2-(pyridin-3-yl)thiophen-3-yl)-N-hydroxyacetamide TFA salt (30g)

$^1$H NMR (400 MHz, CD$_3$OD) δ 1.44 (m, 2H), 1.79 (m, 2H), 2.80 (t, 2H, J=7.2 Hz), 3.54 (s, 2H), 4.40 (t, 2H, J=7.2 Hz), 6.64 (s, 1H), 7.56-7.50 (m, 5H), 7.67 (d, 1H, J=8.0 Hz), 7.73 (d, 1H, J=8.0 Hz), 7.85 (s, 1H), 8.08 (s, 1H), 8.38 (s, 1H), 8.92 (m, 3H).

2-(5-1-(4-Aminobutyl)-2-phenyl-1H-indole-6-carbonyl)-2-(6-fluoropyridin-3-yl)thiophen-3-yl)-N-hydroxyacetamide TFA salt (30h)

$^1$H NMR (400 MHz, CD$_3$OD) δ 1.29 (m, 2H), 1.48 (m, 2H), 2.81 (t, 2H, J=7.2 Hz), 3.49 (s, 2H), 4.39 (t, 2H, J=7.2 Hz), 6.64 (s, 1H), 7.21 (m, 1H), 7.58-7.52 (m, 5H), 7.64 (d, 1H, J=8.0 Hz), 7.72 (d, 1H, J=8.0 Hz), 7.85 (s, 1H), 8.09 (s, 1H), 8.20 (t, 1H, J=6.8 Hz), 8.43 (s, 1H).

2-(5-1-(4-Aminobutyl)-2-phenyl-1H-indole-6-carbonyl)-2-(4-ethylphenyl)-thiophen-3-yl)-N-hydroxyacetamide TFA salt (30i)

$^1$H NMR (400 MHz, CD$_3$OD) δ 1.26 (t, 3H, J=7.6 Hz), 1.46 (m, 2H), 1.78 (m, 2H), 2.73 (q, 2H, J=7.6 Hz), 2.80 (t, 2H, J=7.2 Hz), 3.30 (s, 2H), 4.40 (t, 2H, J=7.2 Hz), 6.65 (s, 1H), 7.37 (d, 2H, J=8.0 Hz), 7.57-7.47 (m, 7H), 7.66 (d, 1H, J=8.2 Hz), 7.74 (d, 1H, J=8.2 Hz), 7.82 (s, 1H), 8.09 (s, 1H).

2-(5-1-(4-Aminobutyl)-2-phenyl-1H-indole-6-carbonyl)-2-(4-methylphenyl)-thiophen-3-yl)-N-hydroxyacetamide TFA salt (30j)

$^1$H NMR (400 MHz, CD$_3$OD) δ 1.46 (m, 2H), 1.78 (m, 2H), 2.35 (s, 3H), 2.80 (t, 2H, J=7.2 Hz), 3.30 (s, 2H), 4.40 (t,

2H, J=7.2 Hz), 6.65 (s, 1H), 7.42 (d, 2H, J=8.0 Hz), 7.62-7.54 (m, 7H), 7.68 (d, 1H, J=8.2 Hz), 7.78 (d, 1H, J=8.0 Hz), 7.82 (s, 1H), 8.02 (s, 1H).

2-(5-1-(4-Aminobutyl)-2-phenyl-1H-indole-6-carbonyl)-2-(4-fluorophenyl)-thiophen-3-yl)-N-hydroxyacetamide TFA salt (30k)

$^1$H NMR (400 MHz, CD$_3$OD) δ 1.48 (m, 2H), 1.80 (m, 2H), 2.81 (t, 2H, J=6.8 Hz), 3.49 (s, 2H), 4.40 (t, 2H, J=6.8 Hz), 6.64 (s, 1H), 7.28 (t, 2H, J=8.4 Hz), 7.61-7.48 (m, 7H), 7.66 (d, 1H, J=8.2 Hz), 7.73 (d, 1H, J=8.2 Hz), 7.81 (s, 1H), 8.08 (s, 1H).

2-(5-1-(4-Aminobutyl)-2-phenyl-1H-indole-6-carbonyl)-2-(4-hydroxyphenyl)-thiophen-3-yl)-N-hydroxyacetamide TFA salt (30l)

$^1$H NMR (400 MHz, DMSO-d$_6$) δ 1.46 (m, 2H), 1.78 (m, 2H), 2.78 (t, 2H, J=7.6 Hz), 3.50 (s, 2H), 4.38 (t, 2H, J=7.6 Hz), 6.65 (s, 1H), 6.90 (d, 2H, J=6.4 Hz), 7.40 (m, 2H), 7.57 (m, 5H), 7.62 (t, 1H, J=7.6 Hz), 7.74 (d, 1H, J=8.2 Hz), 7.79 (s, 1H), 8.06 (s, 1H), 9.00 (s, 1H), 9.94 (s, 1H), 10.98 (s, 1H).

2-(5-1-(4-Aminobutyl)-2-phenyl-1H-indole-6-carbonyl)-2-(3-hydroxyphenyl)-thiophen-3-yl)-N-hydroxyacetamide TFA salt (30m)

$^1$H NMR (400 MHz, CD$_3$OD) δ 1.48 (m, 2H), 1.79 (m, 2H), 2.8 (t, 2H, J=7.6 Hz), 3.54 (s, 2H), 4.42 (t, 2H, J=7.6 Hz), 6.65 (s, 1H), 6.88 (dd, 1H, J=1.6, 8.0 Hz), 6.96 (m, 1H), 7.01 (d, 1H, J=7.2 Hz), 7.32 (t, 1H, J=8.0 Hz), 7.49-7.60 (m, 5H), 7.66 (dd, J=1.0, 8.2 Hz), 7.74 (d, 1H, J=8.2 Hz), 7.81 (s, 1H), 8.10 (s, 1H).

5. Botulinum Neurotoxin Inhibition Assays

Assays of BoNT protease activities were done at 37° C. and contained 0.5 mM substrate, 0.5-1.5 μg/ml recombinant BoNT light chain, 40 mM HEPES, and 0.05% tween, pH 7.3. BoNTA light chain assays also contained 1 mM dithiothreitol, 25 μM ZnCl$_2$, and 0.5 mg/ml bovine serum albumin, while BoNTB light chain assays were supplemented with 1 mM dithiothreitol only. Substrate for BoNTA was a peptide containing residues 187-203 of SNAP-25 (Schmidt, J. J.; Bostian, K. A. J. Protein Chem. 1997, 16, 19), while that for BoNTB was residues 60-94 of VAMP (Shone, C. C.; Roberts, A. K. Eur. J. Biochem. 1994, 225, 263). Inhibitors were dissolved in dimethyl sulfoxide at 10-times the final assay concentration, then diluted into the assay mixture containing substrate, followed by addition of light chain (i.e. inhibitor and light chain concentrations were not preincubated). Assay times and light chain concentrations were adjusted so that less than 10% of the substrate was hydrolyzed. Assays were stopped by acidification with trifluoroacetic acid and analyzed by reverse-phase HPLC as described.

6. Determination of $K_i$

Inhibition of BoNTA light chain by 12 was determined in three independent experiments using eight concentrations of 12 in each. $K_i$ was calculated from slopes of Dixon plots with the equation $K_i = K_m/[(slope)(V_{max})(S)]$, where (S) was the substrate concentration (Segel, I. H. Enzyme kinetics: behavior and analysis of rapid equilibrium and steady state enzyme systems; Wiley: New York, 1975). Kinetic constants for the substrate were taken from reference (Schmidt, J. J.; Stafford, R. G. Appl. Environ. Microbiol. 2003, 69, 297).

7. Protecting Primary Cholinergic Neurons from the Deleterious Effects of Botulinum Neurotoxin Serotype A The primary mouse neuron culture model used has been described previously (Keller et al., 2004, Biochemistry 43:526-532). Briefly, spinal cords were removed from fetal mice at gestation day 13 from timed-pregnant mice. The cords were dissociated with trypsin and primary neurons were plated on Vitrogen 100-coated 24-well tissue culture plates at a density of approximately $10^6$ cells/well. Prior to experimental treatments, the neuron cultures were maintained for 3 weeks at 37° C. in a humidified atmosphere of 90% air and 10% CO$_2$.

The neurotransmitter release assay was performed according to the published method of Sheridan and colleagues (Sheridan et al., 2005, Toxicon 45:377-382; Zhang et al., 2006, Proceedings of the 2006 Bioscience Review, Hunt Valley, Md.). The assay relies on the stimulated release of $^3$H-glycine by 80 mM potassium (K$^+$) as a model for neurotransmitter release. BoNTA blocks glycine release in this assay. A compound may be considered "effective" in the assay if it can prevent or reverse the BoNTA blockade, thereby facilitating release of neurotransmitter from the cultured neurons. Briefly, $^3$H-glycine release is measured in counts per minute (cpm) before, during, and after incubation with 80 mM K$^+$ to ensure that release returns to baseline levels after stimulation. At completion of the experiment, the cells are dissociated and solubilized, and the total protein is measured for each well to normalize for minor variations in the number of cells present in each culture. The $^3$H-glycine release for each well is expressed as cpm per mg of total protein; results for each group are expressed as mean±standard error (SE).

Each assay includes six experimental groups; each group consists of six separate tissue culture wells (total of 36 culture wells):
Group 1: Control stimulated release (80 mM K$^+$-induced $^3$H-glycine release);
Group 2: Maximum effect of BoNTA toxin (treat cells with 10 nM BoNTA; measure 80 mM K$^+$-induced $^3$H-glycine release);
Group 3: Effect of 0.4 mM inhibitor alone (add the inhibitor to cell medium; wash out the excess inhibitor after 4 hr; measure 80 mM K$^+$-induced $^3$H-glycine release);
Group 4. Effect of 0.4 mM inhibitor pre-treatment on BoNTA toxicity (add the inhibitor to cell medium; wash out the excess inhibitor after 4 hr; treat cells with 10 nM BoNTA; measure 80 mM K$^+$-induced $^3$H-glycine release);
Group 5: Effect of 2 mM inhibitor pre-treatment on BoNTA toxicity (add the inhibitor to cell medium; wash out the excess inhibitor after 4 hr; treat cells with 10 nM BoNTA; measure 80 mM K$^+$-induced $^3$H-glycine release);
Group 6: Effect of 0.4 mM inhibitor co-incubation on BoNTA toxicity (add the inhibitor to cell medium; treat cells with 10 nM BoNTA in the presence of the inhibitor; measure 80 mM K$^+$-induced $^3$H-glycine release).

Results

1. Design, Modeling, and Molecular Dynamic Simulations

A computational screen of a chemical database was first carried out to identify molecules capable of coordination with the zinc ion in the active site of the endopeptidase. This screen was performed using an in-house database of 2.5 million chemical structures and the crystal structure of the zinc-bound endopeptidase (Lacy, D. B.; Tepp, W.; Cohen, A. C.; Dasgupta, B. R.; Stevens, R. C. Nat. Struct. Biol. 1998, 5, 898) according to a published protocol (Perola, E.; Xu, K.; Kollmeyer, T. M.; Kaufmann, S. H.; Prendergast, F. G. J. Med. Chem. 2000, 43, 401). It had been reported that the interaction energies between zinc and its coordinates were markedly underestimated by molecular mechanics calculations if the zinc ion was modeled traditionally with a one-atom-zinc representation (Aqvist, J.; Warshel, A. *J. Am. Chem. Soc.* 1990, 112, 2860). To minimize the underestimation that would hamper the search of zinc coordinates, the CaDA approach was used in the screen to estimate the zinc affinities of potential endopeptidase inhibitors.

The top eight compounds identified in the screen were purchased or synthesized and tested as potential inhibitors of the endopeptidase See FIG. 1). Of the eight compounds, compound 1 (FIG. 1) showed 15% inhibition of the endopeptidase at a drug concentration of 100 µM and the remainder showed 5 to 12% inhibition. Competition for zinc coordination by a water molecule or neighboring Glu223 in the active site of the endopeptidase could explain the weak inhibition, as supported by subsequent multiple molecular dynamics simulations (MMDSs) described below.

To address this issue, 20 different molecular dynamics simulations were carried out for each of the eight computer-identified compounds complexed with the endopeptidase. Each of these simulations was carried out for 2.0 ns with a 1.0-fs time step and different initial velocities using the CaDA approach according to a published protocol (Pang, Y.-P. *Proteins.* 2004, 57, 747; Oelschlaeger, P.; Schmid, R. D.; Pleiss, J. *Biochemistry* 2003, 42, 8945). Interestingly, only 1 was able to coordinate zinc throughout all 20 simulations; the others failed to coordinate zinc due to the replacement of the zinc coordinate by either a water molecule or the carboxylate of Glu223. The correlation between the ability to coordinate zinc in computer simulations and the ability to inhibit the endopeptidase in experiments suggested that MMDSs using the CaDA approach are useful in removing those docking-identified compounds that have lower affinities for zinc than water and carboxylate.

The MMDSs showed that compound 1 has a carboxylate coordinating the active-site zinc and a phenyl group interacting with Phe193 of the endopeptidase. This suggested that the affinity of 1 could be improved by strengthening the zinc coordination using better zinc coordinates such as hydroxamates, and its selectivity could be improved by increasing the pi-pi interaction with Phe193 using additional aromatic rings. Thus, analog 2 (FIG. 1) with a hydroxamate group was made. A high-pressure-liquid-chromatography-based (HPLC-based) assay showed that 2 is indeed more active in inhibiting the endopeptidase than 1. Analogs 3-7 (FIG. 1) were made by minor variations of the synthesis of 2. No MMDSs studies were performed on these analogs. In vitro testing revealed that only 4 was more active in inhibiting the endopeptidase than 2. Visual inspection of the MMDS-generated 3D model of the endopeptidase in complex with 1 identified a cavity adjacent to the chlorine-substituted phenyl group of 1. The chlorine-substituted phenyl ring of 1 was thus replaced by 2-phenylindole to make a rod-shaped analog 8 (FIG. 1) to satisfy structural requirements of the endopeptidase inhibitors as suggested by the 3D model of a peptide-substrate-bound endopeptidase, as described above.

MMDSs on the endopeptidase in complex with 8 and its hydroxamic analog 9 (FIG. 1) were performed. The results of these simulations suggested that 8 and 9 were able to fit the active site of the enzyme and coordinate zinc. These compounds were subsequently synthesized and were unexpectedly found to have poor water solubilities. Testing the partially dissolved 8 and 9 showed that both were less potent in inhibiting the endopeptidase than 1 and 2 (FIG. 1).

To increase water solubility and possibly affinity, an aminobutyl group was attached to the indole nitrogen of 9, which led to the design of 12. MMDSs of 12 showed that: (i) the hydroxamate group was able to coordinate the active-site zinc, (ii) the phenyl group substituted at the thiophene ring had a pi-pi interaction with Phe193 and a cation-pi interaction with Arg362, (iii) the indole ring was engaged in a cation-pi interaction with Lys165, (iv) the phenyl group attached to the indole ring has a van der Waals interaction with the side chain of Leu527 and a cation-pi interaction with Lys 165, and (v) the ammonium group interacted with the carboxylates of Glu54 and Glu55. The energetically favorable 3D model of the 12-bound endopeptidase prompted for the synthesis and testing of analogs 10-14 (FIG. 1), where 10 is a synthetic precursor of 12, and 11 is an analog of 12 made by a minor variation of the synthesis of 12 using hydrazine, a known zinc coordinator (Borras, J.; Cristea, T.; Supuran, C. T. *Main Group Met. Chem.* 1996, 19, 339). Analogs 13 and 14 were also made to probe the effect of amino chain length.

2. Synthesis of Compounds

Figure 5:
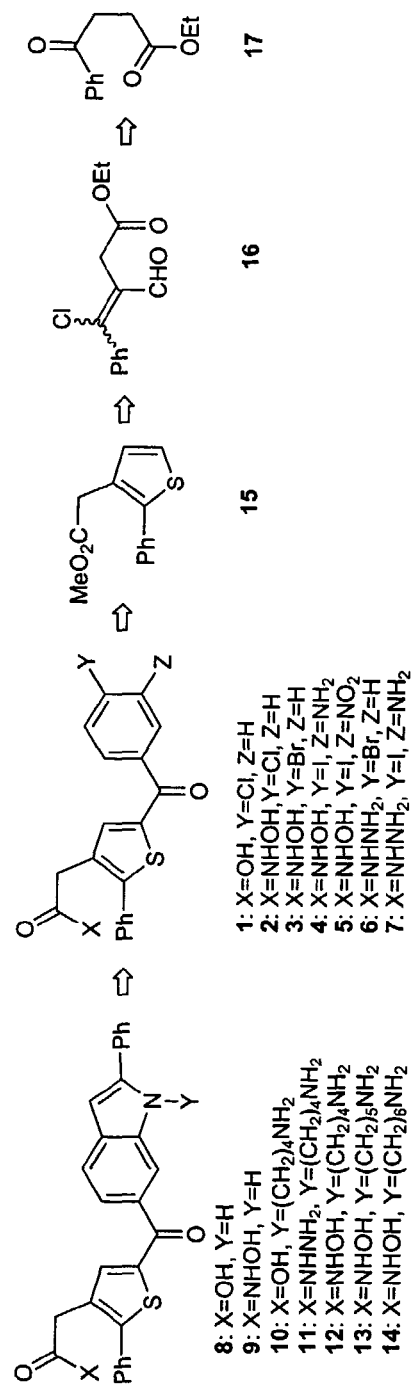
FIG. 5 is a retrosynthetic scheme for the preparation of Compounds 1-14.
Figure 6:
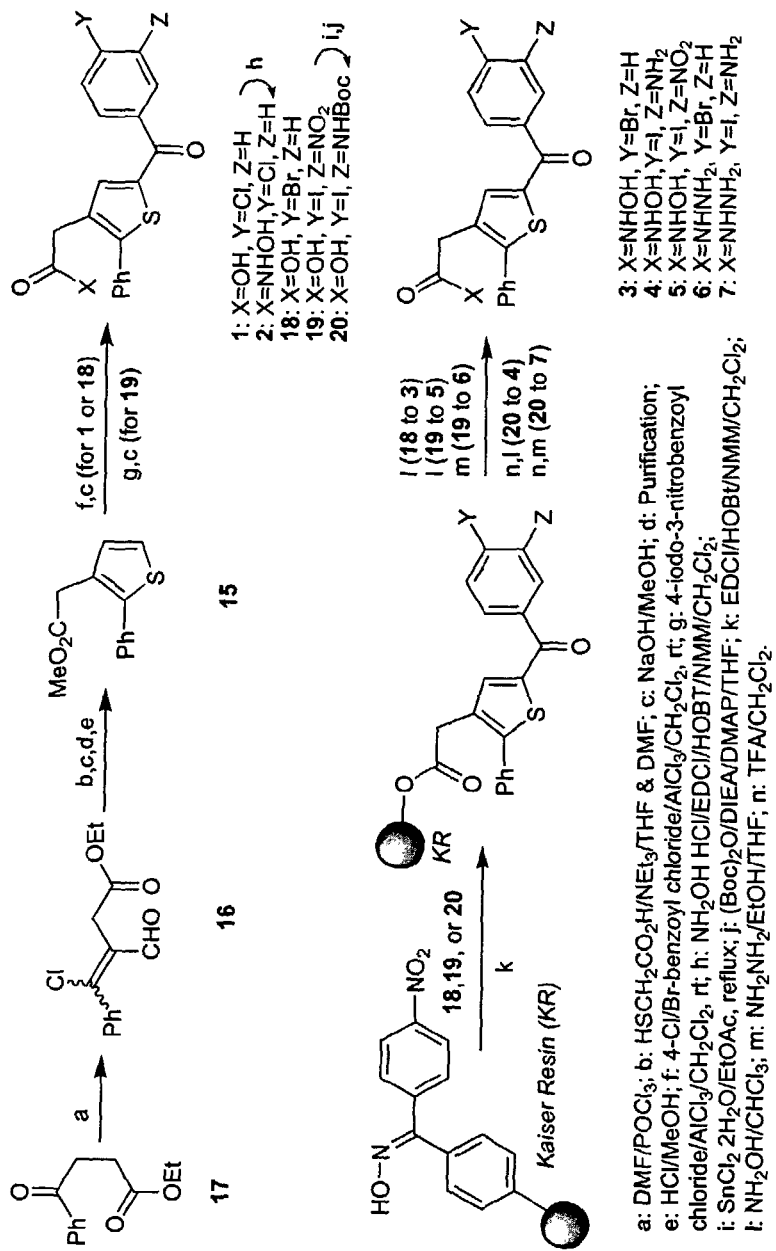
FIG. 6 is a synthetic scheme for the preparation of Compounds 1-7.
Figure 7:
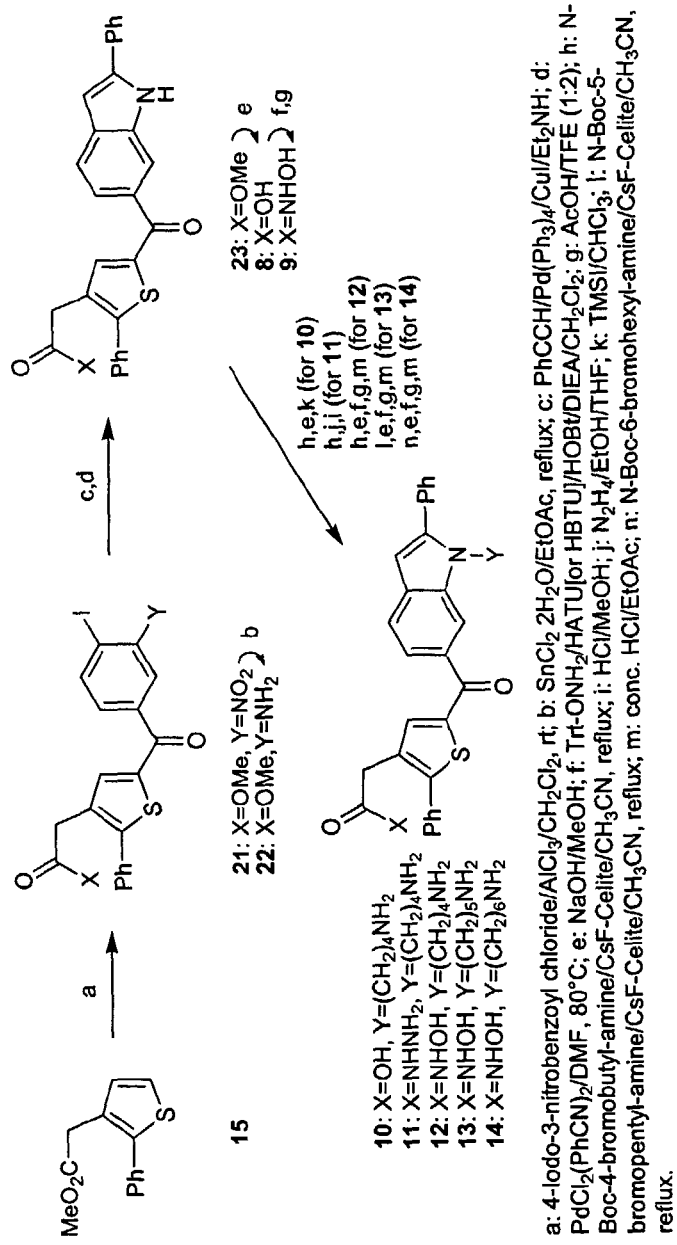
FIG. 7 is a synthetic scheme for the preparation of Compounds 8-14.

The retro synthetic analysis for compounds 1-14 is shown in FIG. 5. Compounds 1-7 and compounds 8-14 were prepared in good yields according to schemes shown in FIGS. 6 and 7, respectively, and as set forth in more detail above and below. Compounds 30 a-m were prepared in good yields according to the scheme shown in FIG. 8 and as described above.

Intermediate 16 was prepared according to a literature procedure (Shvedov, V. I.; Savitskaya, N. V.; Fedorova, I. N. USSR SU753091 1985; Shvedov, V. I.; Fedorova, I. N.; Savitskaya, N. V.; Shvarts, G. Y.; Syubaev, R. D. USSR SU1031165 1985; Shvedov, V. I.; Fedorova, I. N. *J Org. Chem. USSR* 1991, 27, 210). To improve the reported yield for 15, cyclization of 16 to 15 was carried out by the treatment of mercaptoacetic acid and triethylamine in refluxing THF for 4 hours followed by removing THF via distillation and heating at 130° C. in DMF for 18 hours. The cyclization reaction inevitably produced a UV-inactive, sulfur-containing impurity. This impurity interfered with the subsequent Friedel-Crafts reaction and was inseparable from 15 by common purification procedures such as vacuum distillation or column chromatography. This problem was eventually solved by saponification of the ethyl ester group of 15. The resulting acid was separated by filtration from the sulfur-containing impurity and then converted to a methyl ester.

Friedel-Crafts acylation of 15 yielded 1 and intermediates (8 and 19) for making 3-7. In preparing 19, the Friedel-Crafts reaction gave two regio isomers of the thiophene ring. The unwanted minor isomer had a 0.01-ppm-downfield shift for the thiophene proton and was readily removed by chromatography.

Conversion of 19 to 20 was carried out in 95% yield by reduction with stannous chloride, followed by protection of the amine function with $(Boc)_2O$.

Reaction of 1 with hydroxylamine hydrochloride readily gave rise to 2. However, a solid-phase synthesis of hydroxamates using the Kaiser resin (Thouin, E.; Lubell, W. D. *Tetrahedron Lett.* 2000, 41, 457) turned out to be necessary in converting 18-20 to 3-5, respectively. The Kaiser resin also was used to convert 19 and 20 to 6 and 7, respectively.

The indole moiety of 23 was constructed in 61% yield by a two-step literature procedure using $(Pd(PPh_3)_4/CuI/Et_2NH$ and $PdCl_2(PhCN)_2/DMF)$ (Arcadi, A.; Cacchi, S.; Marinelli, F. *Tetrahedron Lett.* 1989, 30, 2581). Precursor 23 was converted to 9 in a high yield by basic hydrolysis followed by coupling with O-tritylhydroxylamine. Deprotection of the trityl group was carried out effectively by using a 1:2 mixture of AcOH/2,2,2-trifluoroethanol.

Introduction of an aminobutyl group to the indole nitrogen of 23 to make 10-14 was initially problematic, presumably due to the poor nucleophilicity of the indole nitrogen and the competition for alkylation at the methylene group under basic conditions. Weak bases such as $K_2CO_3$/DMF, phase-transfer catalyst (PTC), or $K_2CO_3$/18-crown-6 failed to yield the desired product. Ultimately, CsF-Celite/$CH_3CN$ (Hayat, S.; Atta-ur-Rahman; Choudhary, M. I.; Khan, K. M.; Schumann, W. *Tetrahedron* 2001, 57, 9951) was found to be effective in N-alkylation of 23. Precursor 10 was lastly converted to 11 and 12 using hydrazine and O-tritylhydroxylamine, respectively. Analogs 13 and 14 were then made according to the procedure for 12.

Analogs 30a-m were made according to the synthetic scheme shown in FIG. 8, where R is the moieties "a-m" listed at the bottom of the figure.

3. Inhibition Assays

HPLC-based assays were used to measure the inhibition of botulinum neurotoxins (BoNT) by 1-14, as these compounds contain an indole and/or phenyl ring (FIG. 1) that would interfere with fluorescence-based assays of BoNT inhibition (Abbenante, G.; Fairlie, D. P. *Med. Chem.* 2005, 1, 71).

According to the HPLC-based assays, compounds 1-14 demonstrate inhibition of the endopeptidase of BoNTA at the drug concentration of 100 µM, and hydroxamates are more potent than the corresponding carboxylates or hydrazines (FIG. 1). Furthermore, compounds 2, 4 and 12 inhibit the endopeptidase of BoNTA but have no effect on BoNTB (Table 1).

TABLE 1

Inhibition of the endopeptidase (LC) in botulinum neurotoxin serotypes A and B (BoNTA and BoNTB) by hydroxamate-containing inhibitors.

| Inhibitor | % Inhibition at 100 µM | |
| --- | --- | --- |
|  | BoNTA LC | BoNTB LC |
| 2 | 30 ± 1 (2) | 0 |
| 4 | 40 ± 3 (3) | 0 |
| 12 | 96 ± 6 (2) | 0 |

Compounds 12-14 are equally active and they are the most potent of the tested series. Kinetics studies show that the $K_i$ value for the inhibition of the endopeptidase of BoNTA by 12 is 12±2.6 µM (average±standard deviation). Adding more zinc to the assays, up to 0.1 mM, had no effect on the inhibition by 12 (data not shown), confirming that the inhibition was not due to non-specific metal chelation. This is further supported by the finding that 12 did not inhibit the endopeptidase of BoNTB, even when no additional zinc was present. The endopeptidases of BoNTA and BoNTB are closely related. Only two residues are different in the active site between the two enzymes: Phe162 and Phe193 in BoNTA correspond to Asn169 and Ser200 in BoNTB. One might expect, therefore, that the hydroxamate-containing inhibitors of BoNTA would inhibit BoNTB indiscriminately. Interestingly, while a good inhibitor of BoNTA, 12 showed no inhibition on BoNTB (Table 1). Compound 12 is thus a potent and serotype-specific small-molecule inhibitor of the endopeptidase of BoNTA. Further, using the above-described HPLC-based inhibition assay, compounds 12, 30b, 30k, 30a, and 30m showed 48, 50, 67, 72, 77% inhibition of BoNTA at a drug concentration of 15 µM, respectively.

Figure 9:
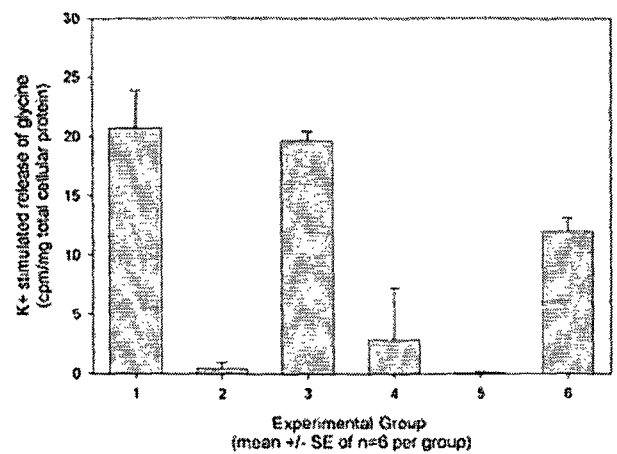
FIG. 9 demonstrates the effect of Compound 30b on Botulinum Neurotoxin Serotype A toxicity as measured by a primary mouse neuron glycine release assay.

4. Protecting Primary Cholinergic Neurons from the Deleterious Effects of Botulinum Neurotoxin Serotype A The result of a cell-based assay is summarized at FIG. 9. Each column is the mean±SE of the six cell wells in each experimental group. The 80 mM $K^+$-induced $^3H$-glycine release for control cells under conditions of this assay was 21±3 cpm (group 1). Treatment with 10 nM BoNTA blocked release to a level of 0.2±0.7 cpm, demonstrating that the toxin was active in the assay (group 2). Compound 30b alone had no measurable effect on glycine release, suggesting the compound does not interfere with the assay endpoint (group 3). When cells were pre-incubated with compound 30b (either 0.4 or 2 mM) and unbound compound removed by wash-out prior to exposure to toxin, there was no statistically significant protection or mitigation of BoNTA intoxication (group 4 or 5 compared by unpaired t-test with group 2). When compound 30b (0.4 mM) was co-incubated with BoNTA in the cell culture medium, it was able to partially antagonize the toxin and to restore glycine release to approximately 55% of control levels of release observed in the absence of toxin (cf., groups 1 and 6). The calculated two-tailed P-value for comparing $^3H$-glycine release/mg protein for BoNTA treated cells with and without co-incubation in 0.4 mM 30b was <0.0001 (group 6 vs. group 2). This experiment shows that appropriate levels of 30b or its derivatives in extracellular fluids are effective at protecting primary cholinergic neurons from the deleterious effects of BoNTA.

CONCLUSIONS

The present work exemplifies the inventions described above through the design, synthesis and testing of a class of small-molecule inhibitors of BoNTA which belong to Formula I. One of these compounds, 12, is a potent and serotype-specific small-molecule inhibitor of BoNTA. Compounds 30a, 30b, 30k, 30m are even more potent inhibitors of BoNTA; compound 30b also shows protection of primary cholinergic neurons from the deleterious effects of BoNTA.

This work demonstrates that the ability of a molecule to coordinate the active-site zinc ion may be governed by, among other things, (i) the fitness of the molecule to the zinc-containing active site, (ii) the intrinsic affinity of the molecule for zinc, and (iii) the competitiveness for zinc coordination relative to nearby zinc ligands available in the active site.

This work suggests that the competitiveness for zinc coordination can be evaluated by MMDSs using the CaDA approach. It is computationally less expensive than a free energy perturbation method, and yet accounts for the entropy and solvent effects in assessing ligands' ability to compete for zinc coordination. Given the identification herein of compound 12 as a serotype-specific and potent small-molecule inhibitor of BoNTA, the CaDA-based MMDS strategy appears to be useful to structure-based design of zinc enzyme inhibitors.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising a compound according to Formula I:

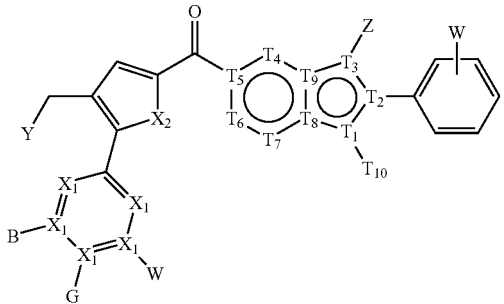

or a pharmaceutically acceptable salt thereof, wherein:

$T_1$-$T_9$ have sp$^2$ hybridization;

$T_3$ is N, and $T_1$-$T_7$ and $T_4$-$T_9$ are C;

wherein $T_{10}$ is W;

each W is selected, independently, from the group consisting of H, NH$_2$, OH, halo, alkyl, alkenyl, alkynyl, alkoxy, alkylthio, cycloalkyl, aryloxy, heteroaryl, heteroalkyl, and heterocyclyl groups having from 1 to 8 C atoms, provided that when W is attached to $X_1$, W is not present when $X_1$ is N;

each $X_1$ is selected, independently, from N and C;

$X_2$ is S, O, or NH;

G is selected from H, halo, NH$_2$, OH, NHR, NRR, S(R), R(NH$_2$), R, and O(R), wherein each R is independently an alkyl group having from 1 to 6 carbon atoms, when the $X_1$ to which G is attached is C; or G is not present when the $X_1$ to which G is attached is N;

B is NHW or G when $X_1$ to which B is attached is C; or not present when $X_1$ to which B is attached is N;

Y is C(=O)NR'OH, CO$_2$H, imidazolyl, SO$_2$NH$_2$, R'SO$_2$NH$_2$, R'SH, or CONR'NH$_2$, wherein R' is H or an alkyl group having from 1 to 6 carbon atoms; and Z is selected from the group consisting of (CH$_2$)$_m$A, (CH$_2$)$_m$NH(CH$_2$)$_n$A, CO(CH$_2$)$_m$A, CO(CH$_2$)$_m$NH(CH$_2$)$_n$A, SO$_2$(CH$_2$)$_m$A, and SO$_2$(CH$_2$)$_m$NH(CH$_2$)$_n$A;

wherein m and n are, independently, an integer from 2 to 14, inclusive;

wherein A is selected from the group consisting of amino, imidazolyl, piperidinyl, piperazinyl, morpholinyl, E1, E2, E3, and E4:

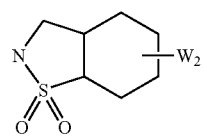   E$_1$

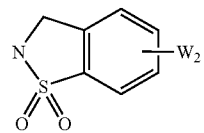   E$_2$

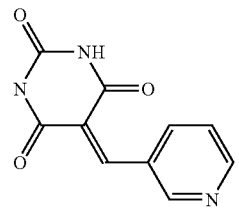   E$_3$

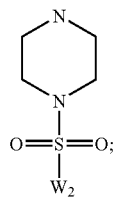   E$_4$ wherein W$_2$ is selected from the group consisting of H, OH, N(R$_1$)(R$_2$), wherein R$_1$ and R$_2$ are, independently, H or alkyl having from 1 to 6 C atoms; and alkyl having from 1 to 6 C atoms.

2. The composition according to claim 1, wherein W is H, OH, NH$_2$, or alkyl having from 1 to 4 C atoms.

3. The composition according to claim 1 or 2, wherein Y is C(=O)NHOH.

4. The composition of claim 1, wherein X$_2$ is S.

5. The composition of claim 1, wherein Z is (CH$_2$)$_m$A, where m is an integer from 1 to 6.

6. The composition of claim 5, wherein A is amino.

7. The composition of claim 1, wherein G is selected from H, F, Cl, Br, NH$_2$, aminoalkyl groups having from 1 to 4 C atoms, OH, and alkylthio and alkoxy groups having from 1 to 4 C atoms.

8. The composition according to claim 1, comprising a compound selected from:

{5-[1-(4-Aminobutyl)-2-phenyl-1H-indole-6-carbonyl]-2-phenylthiophene-3-yl}acetic acid;

{5-[1-(4-Aminobutyl)-2-phenyl-1H-indole-6-carbonyl]-2-phenylthiophene-3-yl}acetic acid hydrazide;

2-{5-[1-(4-Aminobutyl)-2-phenyl-1H-indole-6-carbonyl]-2-phenylthiophene-3-yl}-N-hydroxyacetamide;

2-{5-[1-(5-Aminopentyl)-2-phenyl-1H-indole-6-carbonyl]-2-phenylthiophene-3-yl}-N-hydroxy-acetamide;

2-{5-[1-(6-Aminohexyl)-2-phenyl-1H-indole-6-carbonyl]-2-phenylthiophene-3-yl}-N-hydroxyacetamide hydrochloride;

2-(5-(1-(4-Aminobutyl)-2-phenyl-1H-indole-6-carbonyl)-2-(aminopyridin-4-yl)thiophen-3-yl)-N-hydroxy-acetamide;

2-(5-(1-(4-Aminobutyl)-2-phenyl-1H-indole-6-carbonyl)-2-(pyrimidin-5-yl)thiophen-3-yl)-N-hydroxyacetamide;

2-(5-(1-(4-Aminobutyl)-2-phenyl-1H-indole-6-carbonyl)-2-(2-aminopyrimidin-5-yl)thiophen-3-yl)-N-hydroxyacetamide;

2-(5-(1-(4-Aminobutyl)-2-phenyl-1H-indole-6-carbonyl)-2-(2-(methylthio)pyrimidin-5-yl)thiophen-3-yl)-N-hydroxyacetamide;

2-(5-(1-(4-Aminobutyl)-2-phenyl-1H-indole-6-carbonyl)-2-(2-methoxypyrimidin-5-yl)thiophen-3-yl)-N-hydroxyacetamide;

2-(5-(1-(4-Aminobutyl)-2-phenyl-1H-indole-6-carbonyl)-2-(pyridin-4-yl)thiophen-3-yl)-N-hydroxyacetamide;

2-(5-(1-(4-Aminobutyl)-2-phenyl-1H-indole-6-carbonyl)-2-(pyridin-3-yl)thiophen-3-yl)-N-hydroxyacetamide;

2-(5-(1-(4-Aminobutyl)-2-phenyl-1H-indole-6-carbonyl)-2-(6-fluoropyridin-3-yl)thiophen-3-yl)-N-hydroxyacetamide;

2-(5-(1-(4-Aminobutyl)-2-phenyl-1H-indole-6-carbonyl)-2-(4-ethylphenyl)-thiophen-3-yl)-N-hydroxyacetamide;

2-(5-(1-(4-Aminobutyl)-2-phenyl-1H-indole-6-carbonyl)-2-(4-methylphenyl)-thiophen-3-yl)-N-hydroxyacetamide;

2-(5-(1-(4-Aminobutyl)-2-phenyl-1H-indole-6-carbonyl)-2-(4-fluorophenyl)-thiophen-3-yl)-N-hydroxyacetamide;

2-(5-(1-(4-Aminobutyl)-2-phenyl-1H-indole-6-carbonyl)-2-(4-hydroxyphenyl)-thiophen-3-yl)-N-hydroxyacetamide; and 2-(5-(1-(4-Aminobutyl)-2-phenyl-1H-indole-6-carbonyl)-2-(3-hydroxyphenyl)-thiophen-3-yl)-N-hydroxyacetamide;

or a pharmaceutically acceptable salt thereof.

9. The composition according to claim 8, wherein said compound is selected from:

2-{5-[1-(4-Aminobutyl)-2-phenyl-1H-indole-6-carbonyl]-2-phenylthiophene-3-yl}-N-hydroxyacetamide;

2-(5-(1-(4-Aminobutyl)-2-phenyl-1H-indole-6-carbonyl)-2-(aminopyridin-4-yl)thiophen-3-yl)-N-hydroxyacetamide;

2-(5-(1-(4-Aminobutyl)-2-phenyl-1 H-indole-6-carbonyl)-2-(pyrimidin-5-yl)thiophen-3-yl)-N-hydroxyacetamide;

2-(5-(1-(4-Aminobutyl)-2-phenyl-1H-indole-6-carbonyl)-2-(4-fluorophenyl)-thiophen-3-yl)-N-hydroxyacetamide; and 2-(5-(1-(4-Aminobutyl)-2-phenyl-1H-indole-6-carbonyl)-2-(3-hydroxyphenyl)-thiophen-3-yl)-N-hydroxyacetamide;

or a pharmaceutically acceptable salt thereof.

10. A method of treating or ameliorating one or more symptoms associated with Botulinum toxin poisoning comprising administering a composition according to claim 1 to a mammal.

11. The method of claim 10, wherein the composition comprises 2-{5-[1-(4-Aminobutyl)-2-phenyl-1H-indole-6-carbonyl]-2-phenylthiophene-3-yl}-N-hydroxyacetamide, or a pharmaceutically acceptable salt thereof.

12. The method of claim 10, wherein the composition comprises 2-(5-(1-(4-Aminobutyl)-2-phenyl-1H-indole-6-carbonyl)-2-(pyrimidin-5-yl)thiophen-3-yl)-N-hydroxyacetamide, or a pharmaceutically acceptable salt thereof.

13. The method of claim 10, wherein the composition comprises 2-(5-(1-(4-Aminobutyl)-2-phenyl-1H-indole-6-carbonyl)-2-(3-hydroxyphenyl)-thiophen-3-yl)-N-hydroxyacetamide, or a pharmaceutically acceptable salt thereof.

14. The method of claim 10, wherein said Botulinum toxin is BoNTA, BoNTD or BoNTE.

15. The method of claim 10, wherein said mammal is a human.

16. The method according to claim 10, further comprising administering a trivalent equine antitoxin or penicillin G to said mammal.

17. A method for inhibiting a zinc protease activity comprising: contacting a zinc protease with a compound according to claim 1 wherein said zinc protease is from BoNTA, BoNTD or BoNTE.

18. A kit comprising a composition according to claim 1.

19. The kit of claim 18, wherein said composition is in the form of an injectable composition.

20. An article of manufacture comprising a composition according to claim 1 disposed within a pill, a tablet, a capsule, or a syringe.

* * * * *

UNITED STATES PATENT AND TRADEMARK OFFICE
CERTIFICATE OF CORRECTION

| | | |
|---|---|---|
| PATENT NO. | : 8,492,428 B2 | Page 1 of 1 |
| APPLICATION NO. | : 12/067158 | |
| DATED | : July 23, 2013 | |
| INVENTOR(S) | : Pang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1491 days.

Signed and Sealed this
Third Day of March, 2015

Michelle K. Lee
*Deputy Director of the United States Patent and Trademark Office*